United States Patent
Bachmann et al.

(10) Patent No.: US 11,940,531 B2
(45) Date of Patent: Mar. 26, 2024

(54) CROSSTALK-FREE SOURCE ENCODING FOR ULTRASOUND TOMOGRAPHY

(71) Applicant: THE TRUSTEES OF PRINCETON UNIVERSITY, Princeton, NJ (US)

(72) Inventors: Etienne Bachmann, Trenton, NJ (US); Gregory L. Davies, New York, NY (US); Jeroen Tromp, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 197 days.

(21) Appl. No.: 17/232,642

(22) Filed: Apr. 16, 2021

(65) Prior Publication Data

US 2021/0330287 A1 Oct. 28, 2021

Related U.S. Application Data

(60) Provisional application No. 63/011,369, filed on Apr. 17, 2020.

(51) Int. Cl.
| | | |
|---|---|---|
| *G01S 15/89* | (2006.01) | |
| *A61B 8/00* | (2006.01) | |
| *A61B 8/08* | (2006.01) | |
| *G01S 7/52* | (2006.01) | |

(52) U.S. Cl.
CPC ........ *G01S 15/8977* (2013.01); *A61B 8/5207* (2013.01); *G01S 7/52036* (2013.01); *G01S 15/8952* (2013.01); *G01S 15/8963* (2013.01); *A61B 8/0825* (2013.01); *A61B 8/587* (2013.01); *G01S 7/52052* (2013.01); *G01S 15/8993* (2013.01)

(58) Field of Classification Search
CPC ............. G01S 15/8977; G01S 7/52036; G01S 15/8963; G01S 7/52052; G01S 15/8993; A61B 8/5207; A61B 8/0825; A61B 8/587
See application file for complete search history.

(56) References Cited

U.S. PATENT DOCUMENTS

| | | | | |
|---|---|---|---|---|
| 2004/0099815 | A1* | 5/2004 | Sfez | G01N 21/1717 250/492.1 |
| 2014/0364737 | A1* | 12/2014 | Huang | A61B 8/14 600/447 |
| 2016/0045184 | A1* | 2/2016 | Courtney | A61B 8/4494 600/424 |
| 2016/0066893 | A1* | 3/2016 | Cho | A61B 8/56 600/459 |

(Continued)

FOREIGN PATENT DOCUMENTS

| | | | | |
|---|---|---|---|---|
| WO | WO-2017181201 A1 | * | 10/2017 | A61B 3/0025 |

OTHER PUBLICATIONS

Jeroen Tromp "Source encoding for adjoint tomography", pp. 2019-2044, May 15, 2019.*

(Continued)

*Primary Examiner* — Michael J Dalbo
*Assistant Examiner* — Kaleria Knox
(74) *Attorney, Agent, or Firm* — FOX ROTHSCHILD LLP

(57) ABSTRACT

This disclosure describes systems and methods for crosstalk-free source encoding for ultrasound tomography. This disclosed systems and methods feature real data acquisition acceleration and/or numerical simulation acceleration (or image processing acceleration).

27 Claims, 20 Drawing Sheets

(56) References Cited

U.S. PATENT DOCUMENTS

2019/0083059 A1* 3/2019 Byrnes ............... G16H 30/20
2019/0206576 A1* 7/2019 Shelton, IV ........... G06T 11/60

OTHER PUBLICATIONS

"Source encoding for viscoacoustic ultrasound computed tomographya", Etienne Bachmann; Jeroen Tromp, pp. 3321-3235 (Year: 2020).*

"Coded EXcitation with Spectrum Inversion (CEXSI) for Ultrasound Array Imaging" Yao Wang, Student Member, IEEE, Kurt Metzge, July , pp. 805-823 (Year: 2003).*

"Improved Contrast-Enhanced Ultrasound Imaging With Multiplane-Wave Imaging" Ping Gong, pp. 178-187, Feb. 2018 (Year: 2018).*

Qingchen Zhang "Hybrid-domain simultaneous-source full waveform inversion without crosstalk noise" pp. 1659-1681 (Year: 2018).*

Fabian Kuhn "Ultrasound medical imaging using 2d viscoacoustic full-waveform inversion" pp. 1-128 (Year: 2018).*

Tromp et al: "Source Encoding for Adjoint Tomography", Geophysical Journal International, (2019) 218, 2019-2044, doi: 10.1093/gji/ggz271.

* cited by examiner

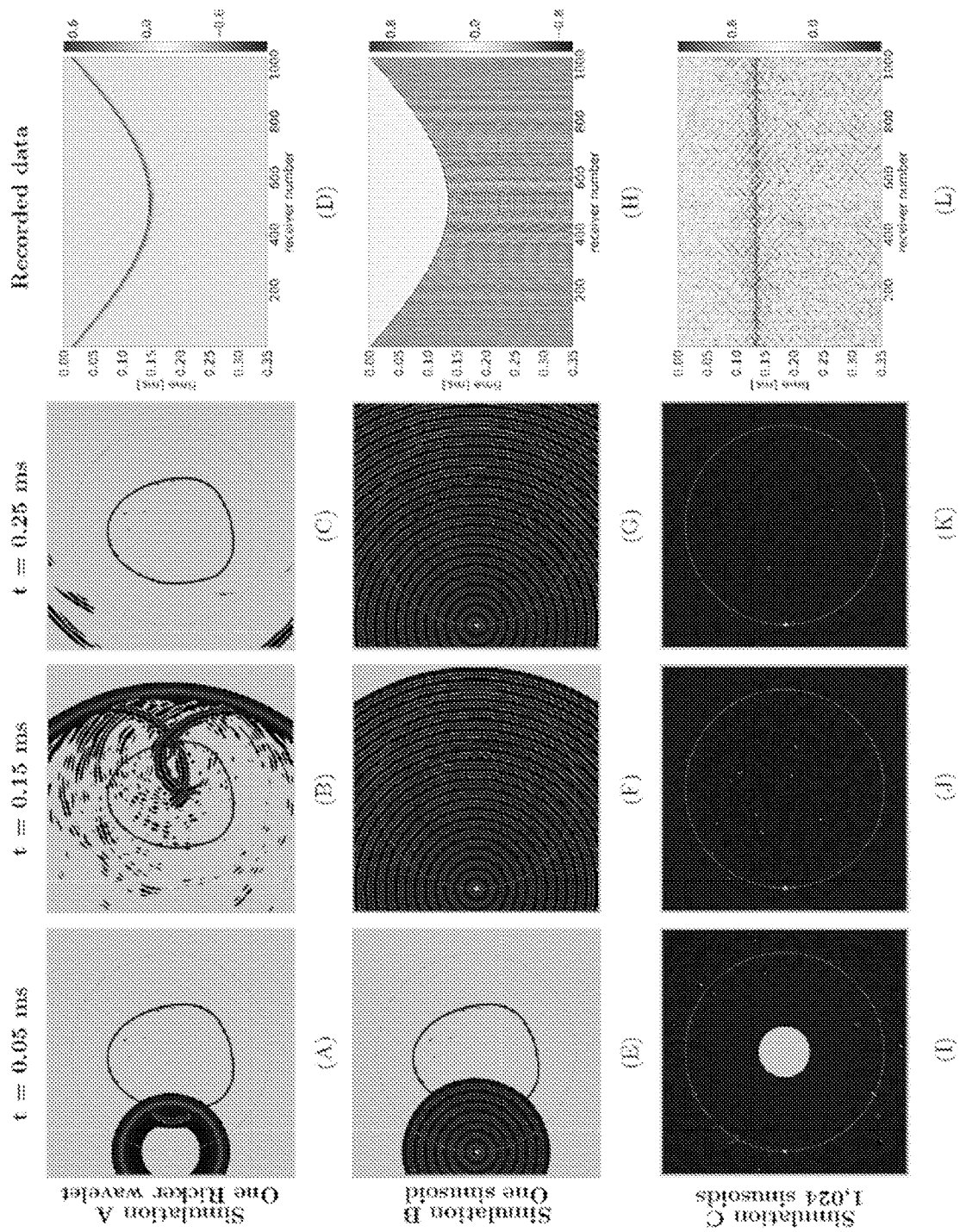
FIGS. 3A, 3B, 3C, 3D, 3E, 3F, 3G, 3H, 3I, 3J, 3K, and 3L

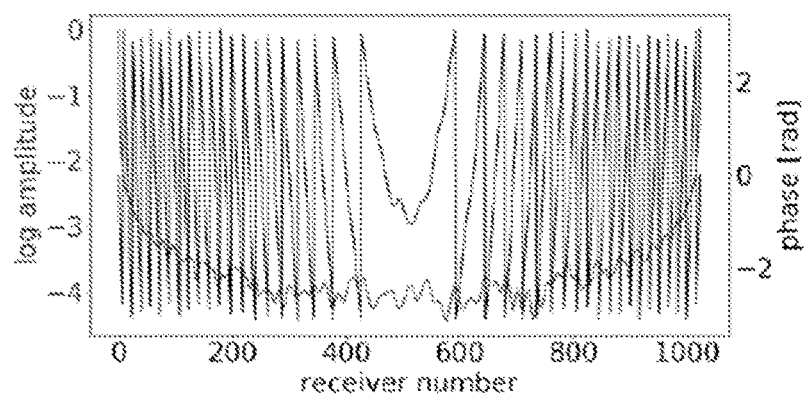
(A) Computed using simulation A
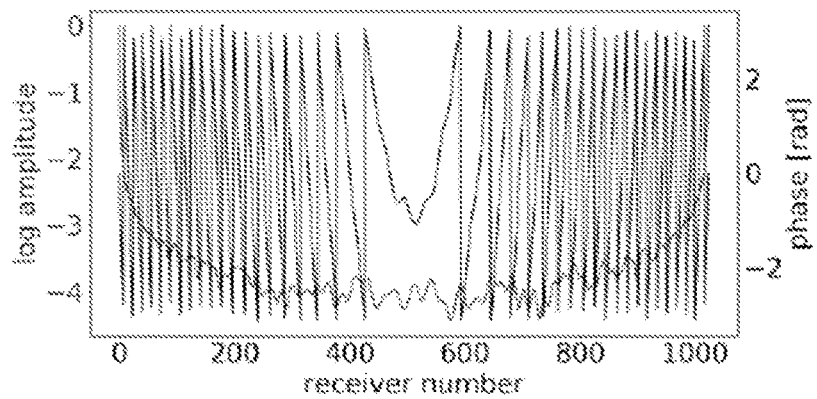
(B) Computed using simulation B
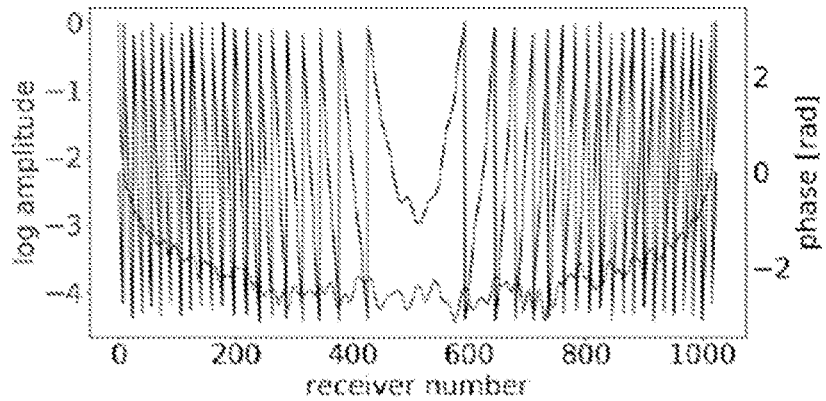
(C) Computed using simulation C
FIGS. 4A, 4B, and 4C

(A) Time domain "super" data (B) Decoded Fourier amplitude of "super" data

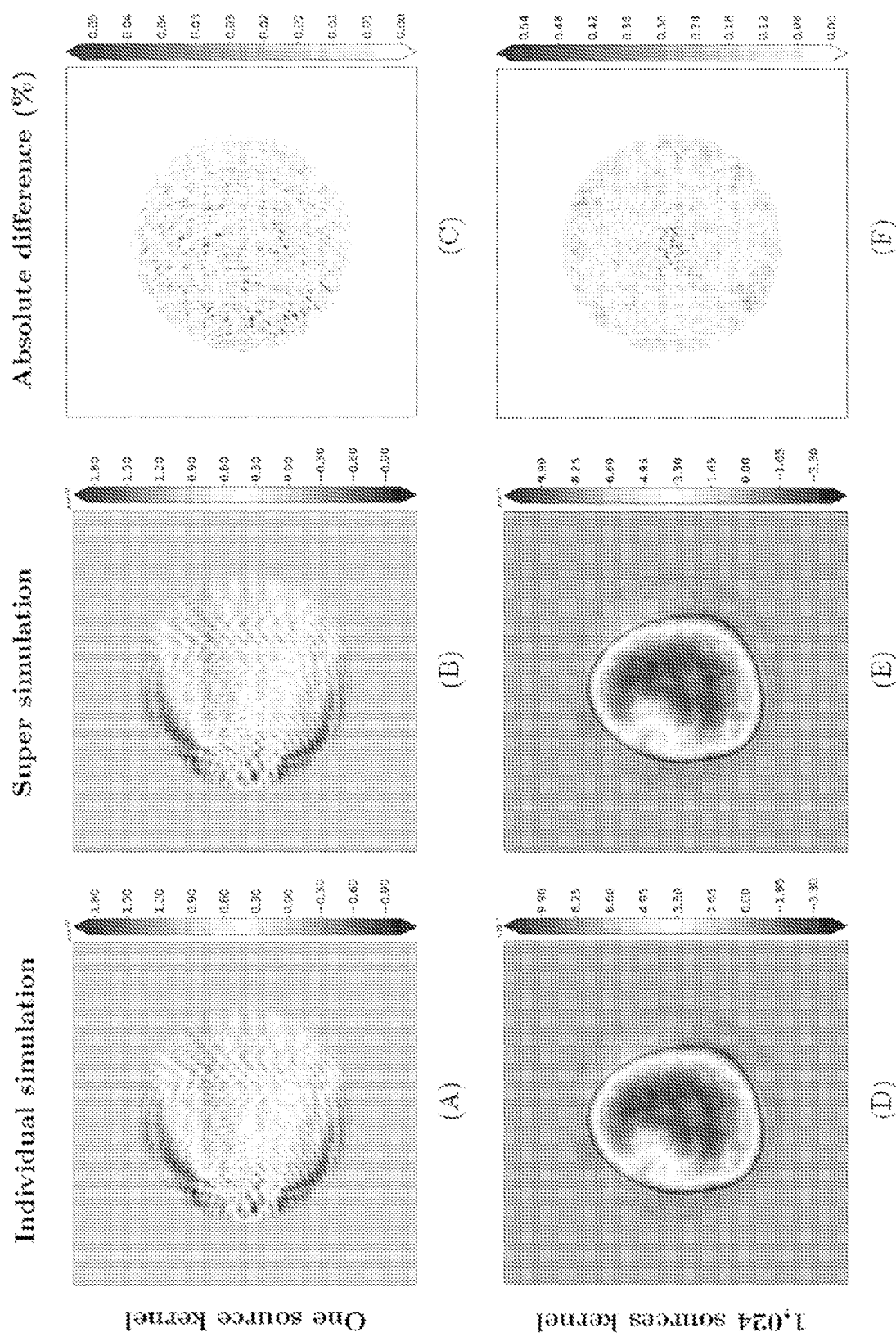
FIGS. 6A, 6B, 6C, 6D, 6E, and 6F (A) Inverted model (90 iterations)

(B) Cost function

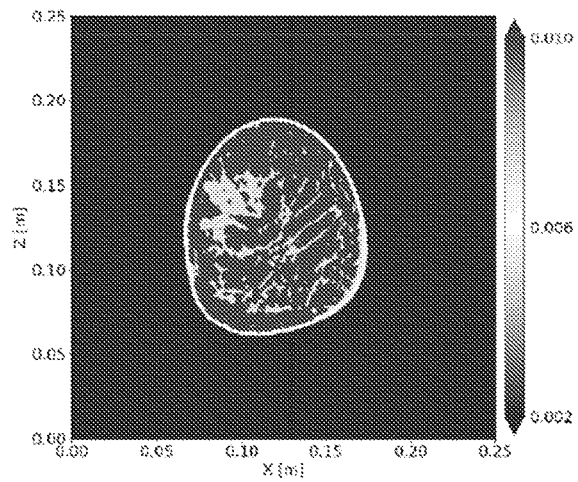
(A) Target $Q_z^{-1}$ map
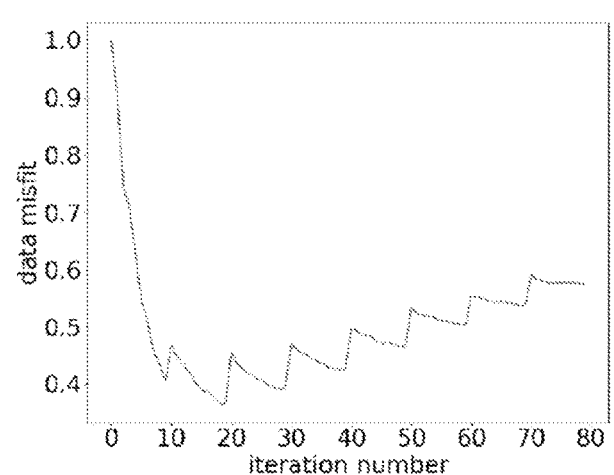
(B) Cost function
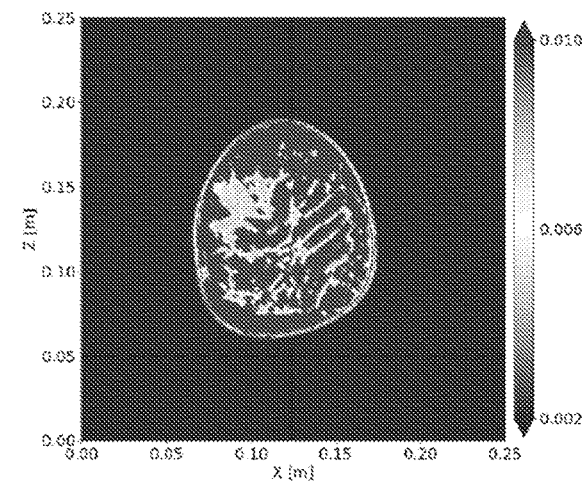
(C)
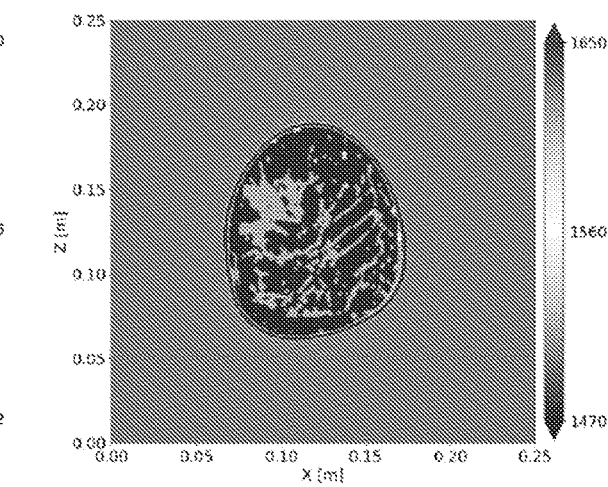
(D)
FIGS. 8A, 8B, 8C, and 8D

(A) Experimental sketch (B) Amplitude of the data spectrum

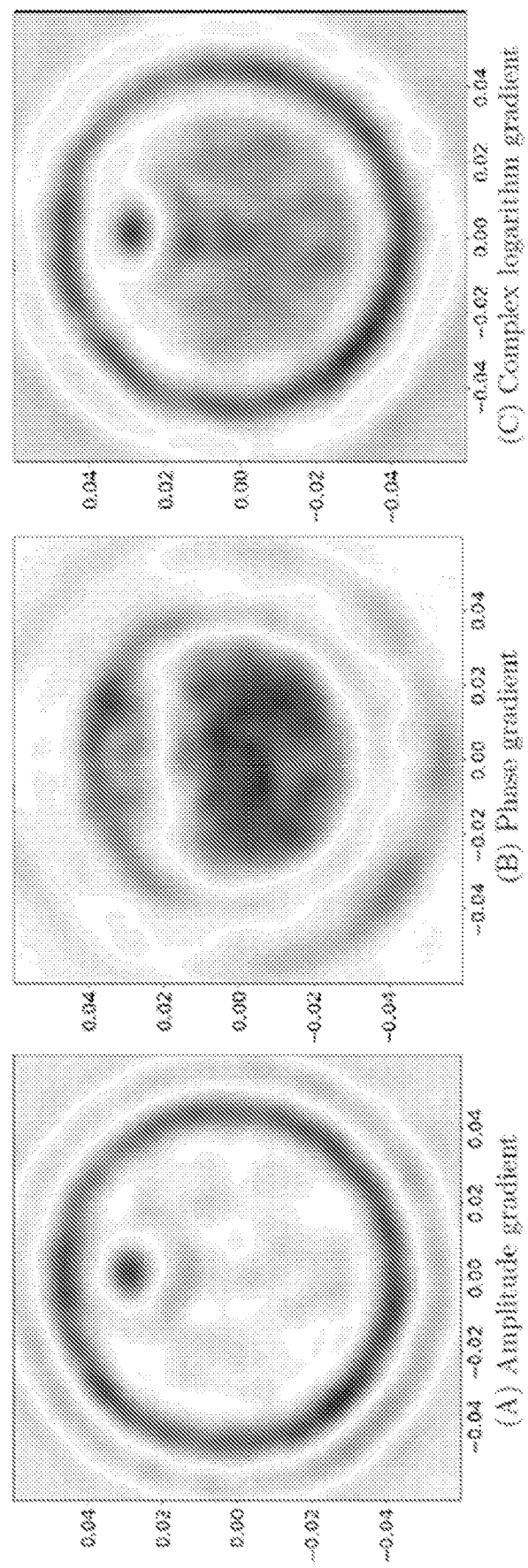
FIGS. 12A, 12B, and 12C

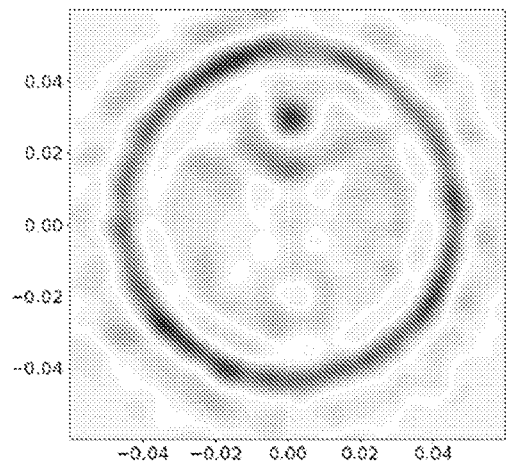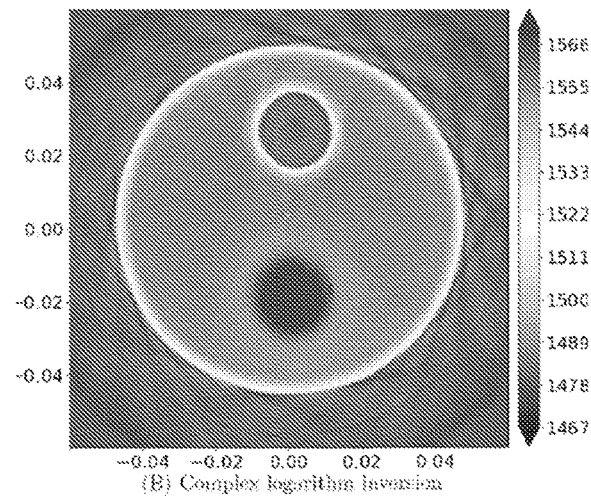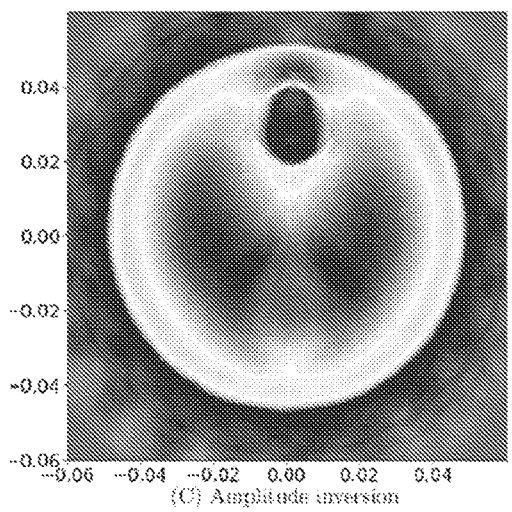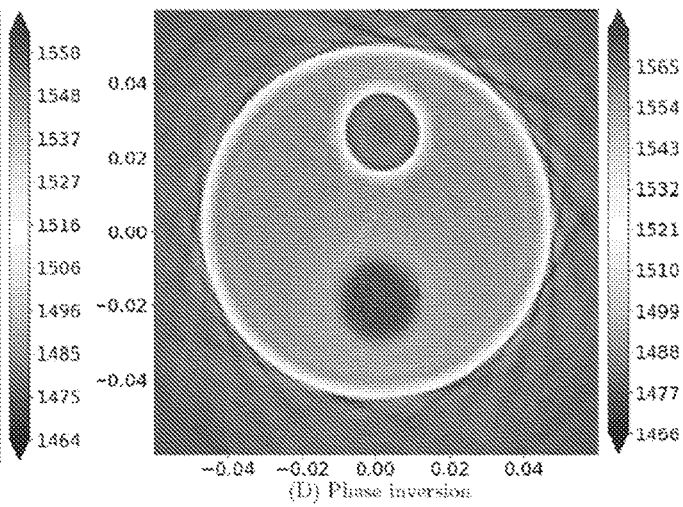
FIGS. 13A, 13B, 13C, and 13D

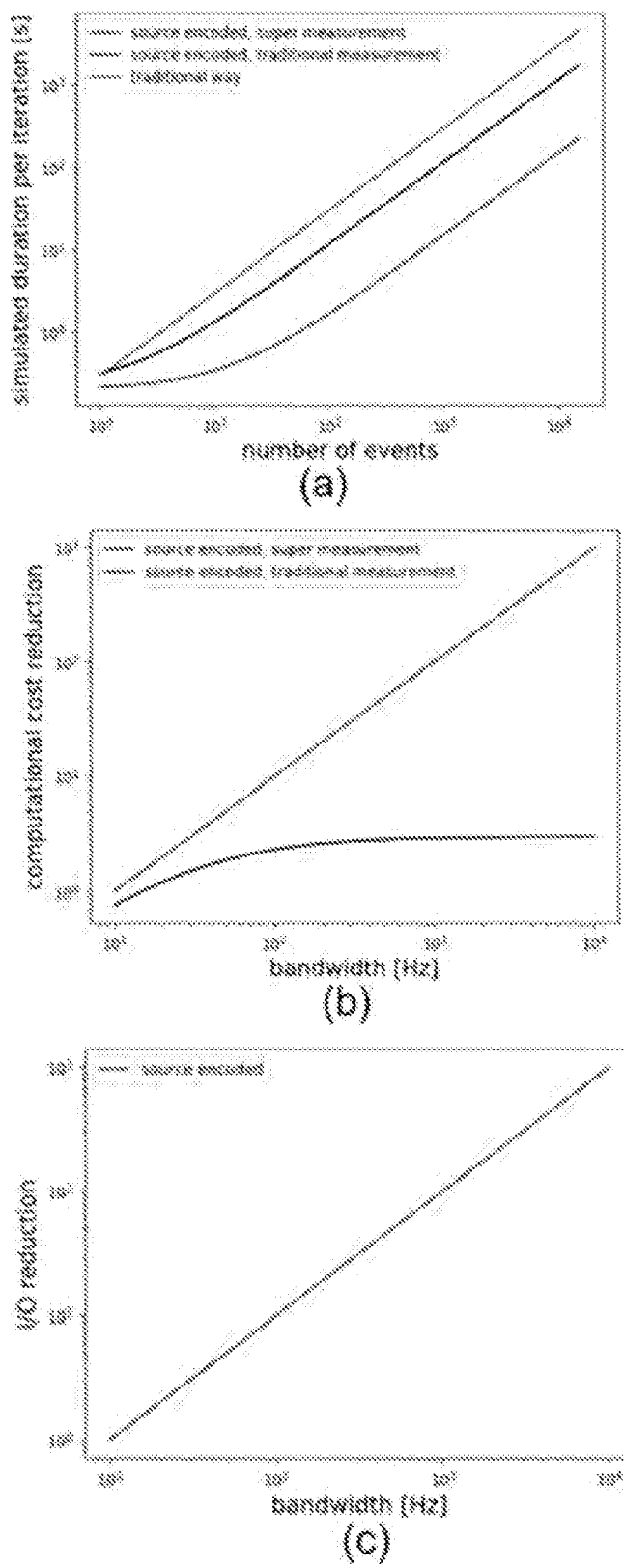
FIGS. 14A, 14B, and 14C

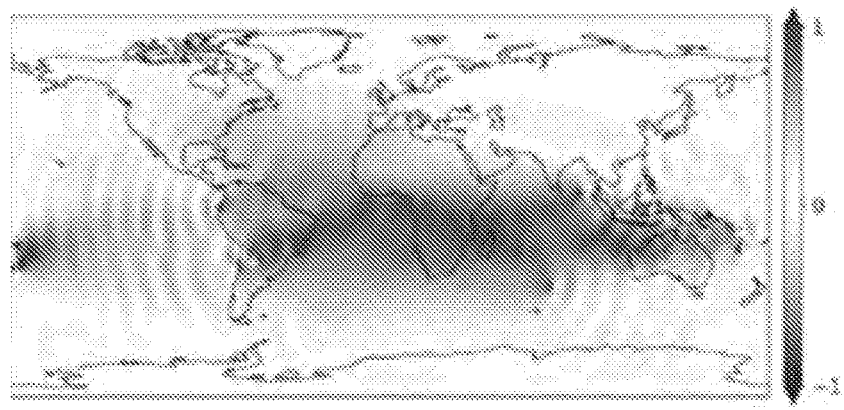
(a) Individual simulation
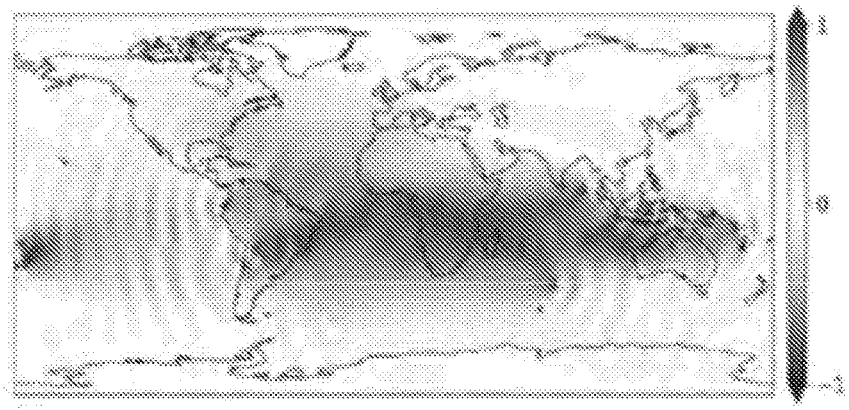
(b) Super simulation
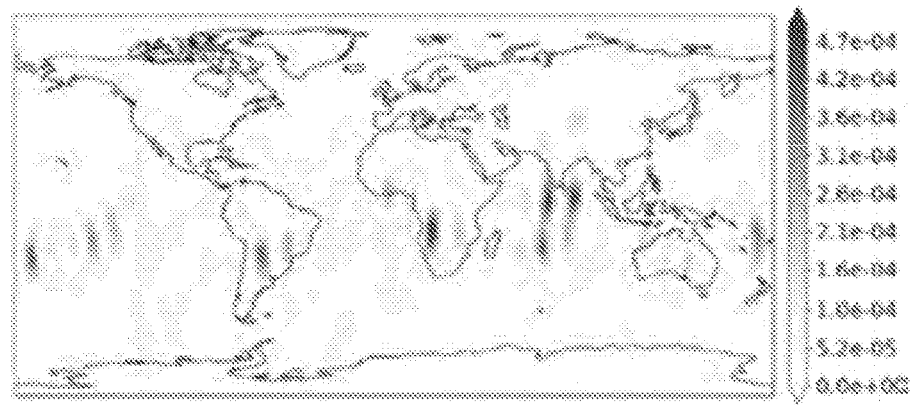
(c) Absolute difference
FIGS. 16A, 16B, and 16C

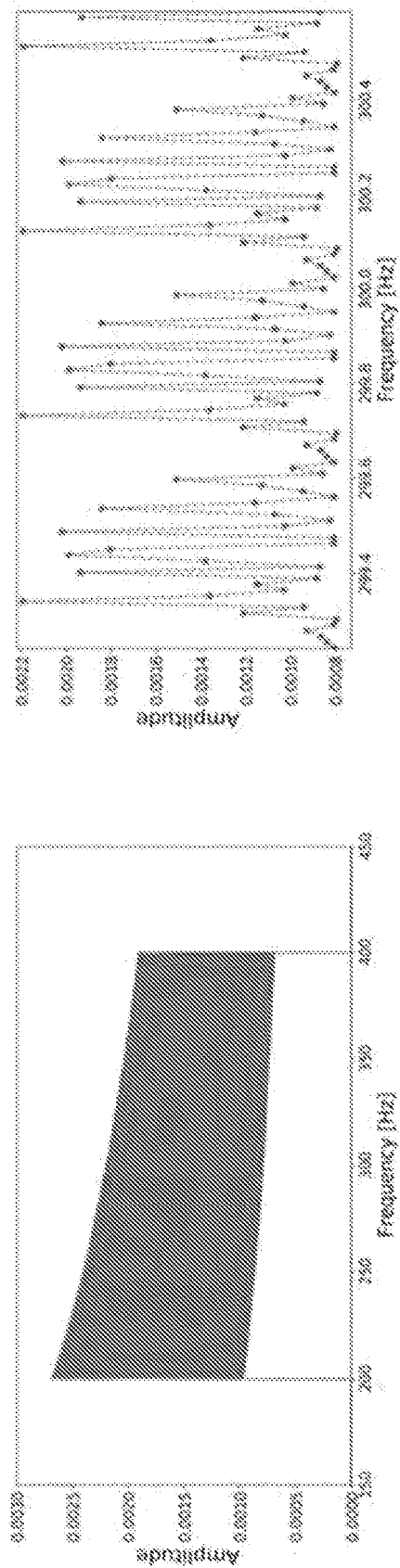
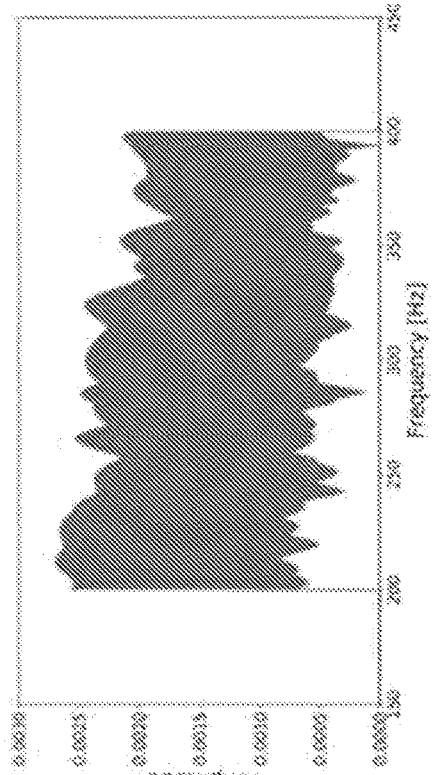
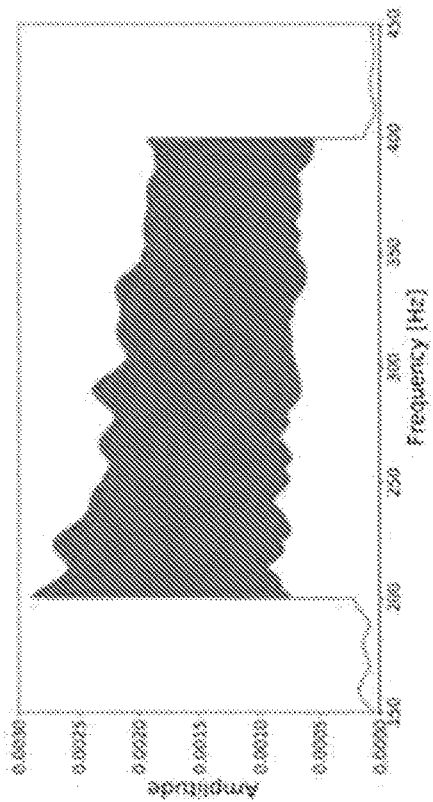
FIGS. 17A, 17B, 17C, and 17D

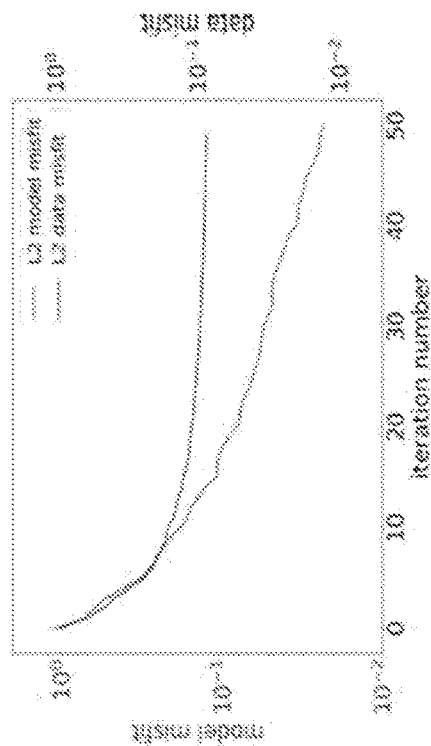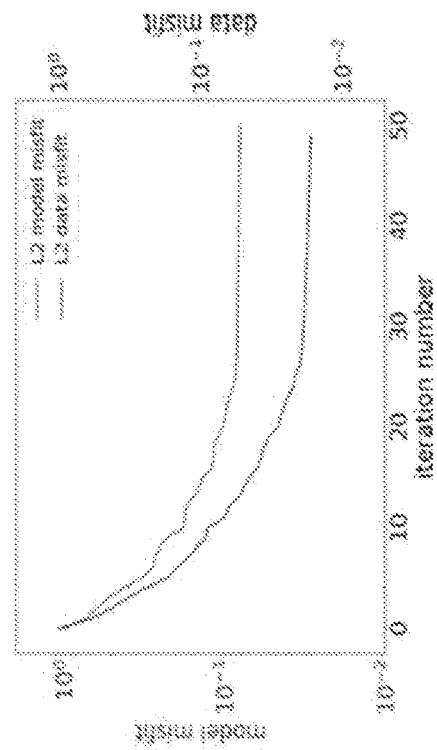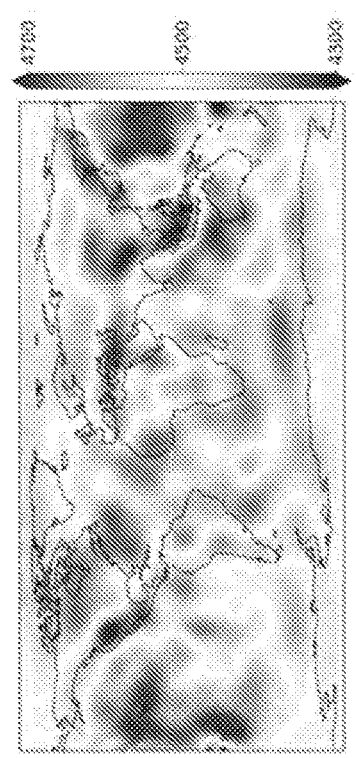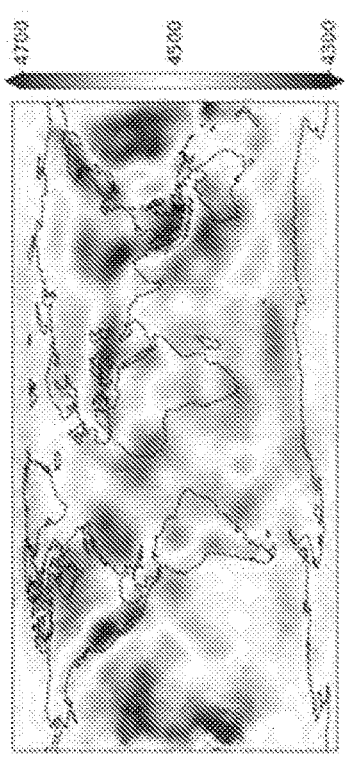
FIG. 18

CROSSTALK-FREE SOURCE ENCODING FOR ULTRASOUND TOMOGRAPHY

CROSS-REFERENCE TO RELATED APPLICATIONS

This application claims priority under 35 U.S.C. § 119(e) to U.S. Provisional Patent Application No. 63/011,369, filed Apr. 17, 2020. The foregoing application is incorporated by reference herein in its entirety.

FIELD OF THE INVENTION

This invention relates to systems and methods for crosstalk-free source encoding for ultrasound tomography.

BACKGROUND OF THE INVENTION

Over the past two decades, Ultrasound Computed Tomography (USCT) has become popular for breast cancer detection. Ray-based solvers have proven to be efficient in this context, and waveform-based inversions have delivered enhanced spatial resolution. The combination of weak out-of-plane scattering, linear transducer arrays, and a large number of ultrasound transmissions has enabled successful two-dimensional (2D) inversions. Despite these advances, the detection of tumors within the entire breast volume requires scanning over numerous stages, resulting in a substantial data acquisition time. Volume reconstruction is based on stacks of 2D images, and spatial resolution is limited by the number of acquired slices and by an averaging effect over the transducer's height. Combining matrix transducer arrays to record data with three-dimensional (3D) wave modeling could mitigate these effects, and fewer data transmissions may be required to sample the entire volume.

In addition to breast cancer screening, detection of prostate cancer with USCT has been investigated, as well as bone and brain tomography. Because these applications involve hard tissues with complex 3D shapes, strong reverberations and diffraction effects are expected, which motivates the use of accurate 3D wave propagation solvers. However, it is well known that 3D waveform inversions come with a significant computational cost, because they involve iterative modeling for each ultrasound transmission. This challenge is mitigated when using frequency-domain solvers, but also becomes computationally expensive when considering large 3D problems.

Thus, there remains a pressing need for novel methods and systems for ultrasound tomography.

SUMMARY OF THE INVENTION

This disclosure addresses the need mentioned above in a number of aspects. In one aspect, this disclosure provides systems and methods for real data acquisition acceleration. In the medical imaging context, for instance, the disclosed systems and methods enhance the patient experience, who has an examination lasting a few seconds instead of ten minutes. From a clinic perspective, this allows examining more patients per day. In particular, emitting ultrasound transducers are excited simultaneously such that they each generate a monochromatic wave at a specific frequency. After enough time, this generates a steady polychromatic wavefield, which can be recorded by receiving ultrasound transducers. As a result, the observed "super" dataset of a given receiving transducer contains useful information coming from each of the emitting sources. Recording must last long enough during the steady state to make deblending possible. The deblending operation may be performed numerically (e.g., on a computer) or with a dedicated hardware system.

In another aspect, this disclosure provides systems and methods for numerical simulation acceleration (or image processing acceleration). In the medical imaging context, for instance, the disclosed systems and methods reduce the duration a radiologist must wait to obtain an image, allowing a given computing machine to process more images per day. The disclosed systems and methods can speed up the computation of simulated "super" dataset. It is the numerical equivalent of the above aspect or real data acquisition acceleration. Only one "super" forward simulation is necessary, instead of S simulations, when considering S sources. The disclosed systems and methods can also speed up the computation of a gradient that includes all S sources contributions. Only two "super" simulations (one forward, one adjoint) are necessary, instead of 2S simulations. After deducing a "super" adjoint source that depends on the cost function, a "super" adjoint simulation can be run. To obtain the gradient, it is possible to cross-correlate, in the time domain, the two super wavefields when both are in a steady state. When doing so, it is no longer necessary to use the deblending formula.

Accordingly, this disclosure provides a system for ultrasound tomography. The system comprises: a plurality of sources configured to transmit waves at one or more frequencies within a frequency bandwidth; one or more receivers configured to receive the waves transmitted by the plurality of sources; and a processor configured to: (a) use a computerized representation of physical property maps of a medium that influence wave propagation; (b) model all the sources and the receivers involved in a dataset; (c) associate to each of the sources a sinusoidal source time function with a defined frequency of a set of frequencies regularly spaced within a bandwidth of interest; and (d) perform a wave propagation simulation where sources are transmitting simultaneously for a time $T_{ss}+k\Delta\tau$, $T_{ss}$ is a simulation duration for simulated wavefield to reach a steady state, where k is an integer $>=1$, and $\Delta_\tau = 1/\Delta f$.

In some embodiments, the system further comprises an ultrasound wave generator configured to associate each of the sources with a defined frequency $f_s$ of a set of frequencies regularly spaced at $\Delta f$ within a $[f_{min}, f_{max}]$ bandwidth.

In some embodiments, the processor is further configured to: (e) receive observed measurements from at least one sensor based on a wave transmitted from at least one source passing through a medium; (f) estimate a frequency-domain observed pressure $\hat{p}_{obs}(x, f_s)$ for each source, where x is a spatial location of a receivers is a $f_s$ is a frequency, associated with source s; (g) evaluate $$\hat{p}_{syn}(x, f_s) = \frac{1}{k\Delta\tau} \int_{T_{ss}}^{T_{ss}+k\Delta\tau} P_{syn}(x, t) e^{-2i\pi f_s(t-T_{ss})}$$

simultaneously for all sources at all receiver positions, where t is time of simulation; and (h) estimate a cost function based on the values of $\hat{p}_{obs}$ and $\hat{p}_{syn}$.

In some embodiments, the processor is further configured to: (i) evaluate the gradient of the cost function for the bulk modulus κ as defined by $$K_\kappa(x) = -\frac{2}{\Delta\tau} \int_{T_{ss}}^{T_{ss}+\Delta\tau} \kappa^{-1}(x) \partial_{t^2} P^\dagger_{syn}(x, T_{ss}+\Delta\tau-t) P_{syn}(x, t) dt,$$

where $P_{syn}^†$ is encoded adjoint wavefield, and $\partial d_{t_2}$ is a second order partial derivative in time, operator.

In some embodiments, the processor is further configured to repeat steps (d) and (g)-(i) to minimize the cost function.

In some embodiments, the defined frequency $f_s = f_{min} + (s-1)\Delta f$ and $$\Delta f = \frac{f_{max} - f_{min}}{S - 1},$$

where s denotes an individual source and S is the total number of sources, $f_s$ is frequency associated with source s, and $[f_{min}, f_{max}]$ is the bandwidth of interest.

In some embodiments, each source is detected by a different subset of sensors. In some embodiments, the waves transmitted from the sources are visco-acoustic waves.

In some embodiments, the simulation comprises at least one forward simulation and adjoint simulation per iteration.

In some embodiments, the processor is further configured to evaluate $$\widehat{p_{syn}}(x_r, f_s; \tau) = \frac{1}{\Delta\tau}\int_\tau^{\tau+\Delta\tau} P_{syn}(x_r, t)e^{-2i\pi f_s(t-\tau)}dt$$

$\forall \{s, r\}, \forall \epsilon, \exists T_{ss}$ such that $\forall \tau > T_{ss}$:

$|\widehat{p_{syn}}(x_r, f_s; \tau) - \widehat{p_{syn}}(x_r, f_s; T_{ss})| < \epsilon$ where s represents a given source simulated in simulation, r represents a given receiver, that records a given source s, $x_r$ is the position of the receiver r, t is time of the simulation, $\tau$ is time after $T_{ss}$, Psyn is a wavefield simulated by a solver, $f_s$ is a frequency associated with source s, and $\epsilon$ can be any value.

In some embodiments, wherein the processor is further configured to compute a gradient of the cost function represented by:

$$\chi_W(m) = \frac{1}{2}\sum_{s=1}^{S}\sum_{r=1}^{R_s}|\widehat{p_{syn}}(x_r, f_s; m) - \widehat{p_{obs}}(x_r, f_s)|^2$$

where m is a wavespeed, density, attenuation map, or a combination, $\widehat{P_{syn}}$ the Fourier transform of the wavefield $P_{syn}$, and $\widehat{P_{obs}}$ is the Fourier transform of the observed wavefield $P_{obs}$.

In some embodiments, the cost function comprises a source-encoded cost function that integrates contributions from all the sources. In some embodiments, the cost function comprises waveform differences, phase and amplitude measurements, double-difference phase and amplitude measurements, cross-correlation traveltime measurements, or a generic adjoint tomography cost function.

In some embodiments, the system comprises an ultrasound device. In some embodiments, the medium comprises human tissue or soil. In some embodiments, the processor is further configured to generate an image representation of the medium.

Also provided in this disclosure is a method for ultrasound tomography. The method comprises: (i) using a computerized representation of physical property maps of a medium that influence wave propagation; (ii) modeling all the sources and the receivers involved in a dataset; (iii) associating to each of the sources a sinusoidal source time function with a defined frequency of a set of frequencies regularly spaced within a bandwidth of interest; and (iv) performing a wave propagation simulation where sources are transmitting simultaneously for a time $T_{ss} + k\Delta\tau$, where $T_{ss}$ is a simulation duration for simulated wavefield to reach a steady state, k is an integer $\geq 1$, and $\Delta T = 1/\Delta f$.

In some embodiments, the method further comprises associating each of the sources with a defined frequency $f_s$ of a set of frequencies regularly spaced at $\Delta f$ within a $[f_{min}, f_{max}]$ bandwidth.

In some embodiments, the method further comprises: (v) receiving observed measurements from at least one sensor based on a wave transmitted from at least one source passing through a medium; (vi) estimating a frequency-domain observed pressure $P_{obs}(x, f_s)$ for each source, where x is a spatial location of a receiver, $f_s$ is a frequency associated with source s; (vii) evaluating $$\hat{p}_{syn}(x, f_s) = \frac{1}{k\Delta\tau}\int_{T_{ss}}^{T_{ss}+k\Delta\tau} P_{syn}(x, t)e^{-2i\pi f_s(t-T_{ss})}$$

simultaneously for all sources at all receiver positions, where t is time of simulation; and (viii) estimating a cost function based on the values of $\hat{P}_{obs}$ and $\hat{P}_{syn}$.

In some embodiments, the method further comprises (ix) evaluating the gradient of the cost function for the bulk modulus $\kappa$, as defined by $$K_\kappa(x) = -\frac{2}{\Delta\tau}\int_{T_{ss}}^{T_{ss}+\Delta\tau}\kappa^{-1}(x)\partial_{t^2}P_{syn}^†(x, T_{ss} + \Delta\tau - t)P_{syn}(x, t)dt,$$

$P_{syn}^†$ is an encoded adjoint wavefield, and $\partial_{t_2}$ is a second order partial derivative in time, operator.

In some embodiments, the method further comprises repeating steps (iv) and (vii)-ix) to minimize the cost function.

In some embodiments, the defined frequency $f_s = f_{min} + (s-1)\Delta f$ and $$\Delta f = \frac{f_{max} - f_{min}}{S - 1},$$

where s denotes an individual source and S is the total number of sources, $f_s$ is frequency associated with source s, and $[f_{min}, f_{max}]$ is the bandwidth of interest.

In some embodiments, each source is detected by a different subset of sensors. In some embodiments, the waves transmitted from the sources are visco-acoustic waves.

In some embodiments, the simulation comprises at least one forward simulation and adjoint simulation per iteration.

In some embodiments, the method further comprises evaluating $$\widehat{p_{syn}}(x_r, f_s; \tau) = \frac{1}{\Delta\tau}\int_\tau^{\tau+\Delta\tau} P_{syn}(x_r, t)e^{-2i\pi f_s(t-\tau)}dt$$

$\forall \{s, r\}, \forall \epsilon, \exists T_{ss}$ such that $\forall \tau > T_{ss}$:

$|\widehat{p_{syn}}(x_r, f_s; \tau) - \widehat{p_{syn}}(x_r, f_s; T_{ss})| < \epsilon$ where s represents a given source simulated in simulation, r represents a given receiver, that records a given source s, $x_r$ is the position of the receiver r, t is time of the simulation, $\tau$ is time after $T_{ss}$, Psyn is a wavefield simulated by a solver, $f_s$ is a frequency associated with source s, and $\varepsilon$ can be any value.

In some embodiments, the method further comprises computing a gradient of the cost function represented by:

$$\chi_W(m) = \frac{1}{2} \sum_{s=1}^{S} \sum_{r=1}^{R_s} |\widehat{P_{syn}}(x_r, f_s; m) - \widehat{P_{obs}}(x_r, f_s)|^2$$

where m is a wavespeed, density, attenuation map, or a combination, $\widehat{P_{syn}}$ the Fourier transform of the wavefield $P_{syn}$, and $\widehat{P_{obs}}$ is the Fourier transform of the observed wavefield $P_{obs}$. In some embodiments, the cost function comprises a source-encoded cost function that integrates contributions from all the sources. In some embodiments, the cost function comprises waveform differences, phase and amplitude measurements, double-difference phase and amplitude measurements, cross-correlation traveltime measurements, or a generic adjoint tomography cost function.

In some embodiments, the medium comprises human tissue or soil. In some embodiments, further comprising generating an image representation of the medium.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

FIGS. 3A, 3B, 3C, 3D, 3E, 3F, 3G, 3H, 3I, 3J, 3K, and 3L (collectively "FIG. 3") are a set of diagrams showing three simulations of wave propagation in the model shown in FIG. 2 illustrated with snapshots and recorded data. FIGS. 3A, 3B, 3C, and 3D show Simulation A: One source transmitting a Ricker source-time function (STF) centered at 150 kHz. The full frequency spectrum is modeled. FIGS. 3E, 3F, 3G, and 3H show Simulation B: One source transmitting a sine STF at 150 kHz. It was observed in the recorded data that after approximately 0.15 ms of transient state, a monochromatic steady state is established for any recording transducer position. FIGS. 3I, 3J, 3K, and 3L show Simulation C: All 1,024 transducers are simultaneously transmitting, each using a sine STF at a specific frequency as described in Eq. (6), over the [50-254.8] kHz bandwidth. The source labeled by the yellow star emits a sine STF at 150 kHz. For each of these simulations, the Green function can be accurately evaluated at 150 kHz of the source labeled by the yellow star anywhere in the domain.

FIGS. 4A, 4B, and 4C (collectively "FIG. 4") are a set of diagrams showing numerical tests of "decoding" using the orthogonality of the Fourier basis, computed using Simulations A (FIG. 4A), B (FIG. 4B), C (FIG. 4C), respectively. Shown is the Green function at 150 kHz for the source labeled by the yellow star in FIG. 3 at all receiver positions for each of the three simulation types. Fourier coefficients for simulation A (FIG. 4A) are computed using Eq. (2). Fourier coefficients for simulations B and C (FIGS. 4B and 4C) are computed using Eq. (10). The maximum phase discrepancy between simulations A and C data (FIGS. 4A and 4C) is 0.05% over all the receivers. The corresponding maximum amplitude discrepancy is 0.1%.

FIGS. 6A, 6B, 6C, 6D, 6E, and 6F (collectively "FIG. 6") are a set of diagrams showing a numerical test of orthogonality to compute "super" Fréchet derivatives from 1,024 sources. Each image is masked such that derivatives are zero far from the region of interest (ROI). FIGS. 6A and 6B show Fréchet derivative due to the source labeled by the star in FIG. 3, with 150 kHz measurements. Eq. (22) is used to compute these derivatives, because the frequency domain is the only suitable option to extract them from a super simulation. FIG. 6C shows the absolute difference between FIG. 6A and FIG. 6B, which has a maximum of 0.05% over the ROI. FIGS. 6D and 6E show summed Frechet derivative of 1,024 monochromatic sources over the [50-254.8] kHz bandwidth, computed without decoding using Eq. (21); FIG. 6D requires 2,048 monochromatic source simulations, while FIG. 6E uses only two super simulations. FIG. 6F shows the absolute difference between FIG. 6A and FIG. 6B, with a maximum of 0.54% over the ROI.

FIGS. 8A, 8B, 8C, and 8D (collectively "FIG. 8") are a set of diagrams showing joint wavespeed and attenuation (Vp–$Q_k^{-1}$) inversion result. FIG. 8A shows target $Q_k^{-1}$ map. Q0 ranges between 100 and 500. FIG. 8B shows evolution of the cost function as a function of iterations. FIGS. 8C and 8D show inverted maps. 80 iterations were performed in 85 minutes using a single GPU.

FIGS. 12A, 12B, and 12C (collectively "FIG. 12") are a set of diagrams showing gradients obtained with different cost functions, with data from the [50-450] kHz bandwidth and a homogeneous synthetic model. Their observation reveals the sensitivity of each measurement: amplitude mostly highlights the interfaces (FIG. 12A) while phase shows the global structure of the medium (FIG. 12B). A complex logarithm is sensitive to both interfaces and structure features by combining phase and amplitude data (FIG. 12C).

FIG. 13A shows a gradient obtained using the same conditions as in FIG. 12C, but using the "local" double difference cost function, as defined in Eq. (14). A significant difference from FIG. 12C due to information removal was observed. FIGS. 13B, 13C, and 13D are a set of diagrams showing inversion results obtained with "local" double difference cost functions, with inverted data in the [50-5,000] kHz bandwidth. Only local pairs of stations are compared in order to mitigate the point source approximation. While FIG. 13B and FIG. 13D converged, the amplitude inversion FIG. 13C got trapped in a local minimum.

FIGS. 14A, 14B, and 14C (collectively "FIG. 14") are a set of diagrams showing potential speed-up depending on measurement type and allocated frequency bandwidth. It was assumed a simulation per event of duration T=0.1 s and a bandwidth of 200 Hz, which reflects the model setup shown in FIG. 15. As a reasonable assumption, we set $T_{ss} \approx T$ FIG. 14A shows simulation costs for traditional inversions, source-encoded inversions, and source-encoded inversions with traditional measurements. Because super measurements are possible, one can expect a 20× speed-up in this configuration. FIG. 14B shows computational cost reduction relative to a traditional inversion for source-encoded inversions and source-encoded inversions with traditional measurements, that is, the difference between the blue curve and the other two curves shown in FIG. 14A. The expected computational cost reduction from source encoding was observed, which corresponds to the asymptotic behavior of the curves in FIG. 14A. Because time domain measurements require an individual simulation for each event, no speed-up bigger than a factor of 3 can be expected. FIG. 14C shows I/O reduction based on Eq. (85). Whether conventional or super measurements are considered, I/O is drastically reduced when considering a larger bandwidth.

FIGS. 16A, 16B, and 16C (collectively "FIG. 16") are a set of diagrams showing the absence of crosstalk between encoded sources in the time domain. FIG. 16A shows a traditional approach with kernel computation in the time domain. FIG. 16B shows a source-encoded approach in which the gradient is calculated in the time domain based on Eq. (70). The two gradients are rescaled in the range [−1, +1] using a common factor. The small differences as shown in FIG. 16C prove that frequency-domain decoding is not necessary to compute the supersensitivity kernel, thanks to the mathematical equivalence of Eqs. (70) and (72). The largest discrepancy between the two gradients over the entire domain is 0.048 percent.

FIGS. 17A, 17B, 17C, and 17D (collectively "FIG. 17") are a set of diagrams showing the results of a study of the impact of approximations on decoding. A randomly selected seismogram was used, involving a super simulation encoding 16.384 frequencies in the [200;400] Hz range. The simulation lasts 1640400 time steps, including 2000 time steps of a transient state (defining $T_{SS}$) and 1638400 time steps of steady-state (defining $\Delta\tau$). FIG. 17A shows a correctly decoded seismogram. The progressive decrease of the Fourier amplitude with increasing frequency was observed, which matches the theoretical expectation $A(\omega) \propto 1/\sqrt{\omega}$. FIG. 17B shows a zoom-in on a narrow frequency subinterval of FIG. 17A to observe individual contributions of each event. Every event uses 512 frequencies, spaced such that the same event is encoded every 32 consecutive frequencies. As expected, we obtain a periodic signal (repeating itself every 32 samples) and clearly distinguish the contribution of each event, further demonstrating orthogonality. FIG. 17C shows an (incorrect) time interval of 1638390 time steps is used to decode, which leads to failure, because the wrong frequencies are evaluated and the orthogonality condition is not satisfied. FIG. 17D shows decoding performed over a time interval containing 1000 time steps of the transient state. Because the evaluated signal is no longer a pure trigonometric polynomial, orthogonality is lost, also resulting in incorrect decoding.

FIG. 18 shows a comparison between the usual full spectrum inversion and the source encoded inversion. The encoded version uses 32 frequencies, one per event, in the [200;400] Hz bandwidth. Global convergence is achieved in both cases, even if some extra oscillations can be observed in the source encoded version. This is due to the drastic reduction of the frequency content of the inverted data, which can be mitigated.

DETAILED DESCRIPTION OF THE INVENTION

Figure 1A:
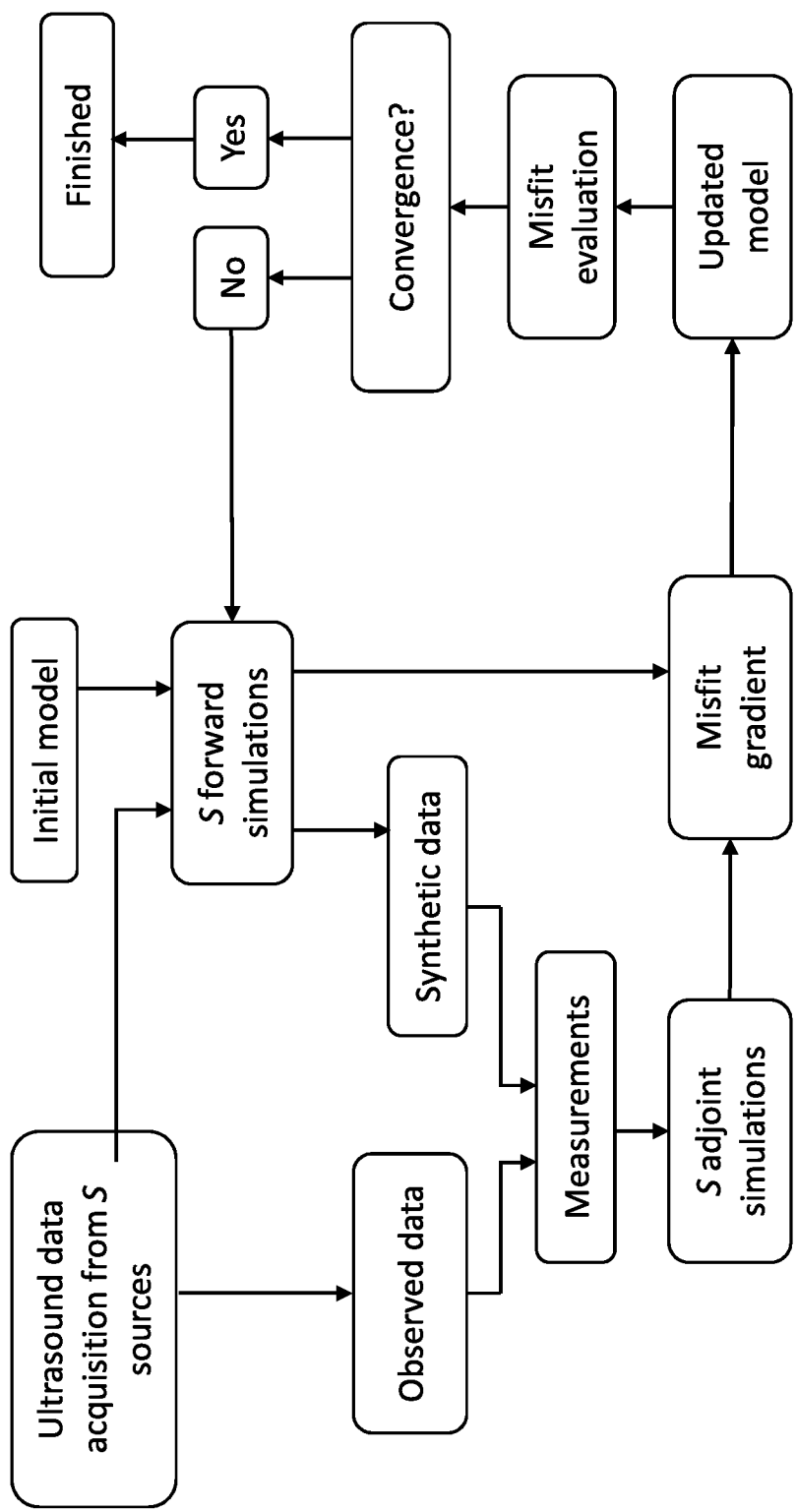
FIG. 1A shows a flowchart illustrating classical waveform inversion.

This disclosure describes crosstalk-free source encoding for ultrasound tomography. The disclosed approach allows for, for example, rapid image reconstruction using full waveform inversion (FWI) and rapid acquisition of experimental signals, an improvement of existing methods. More particularly, in one use for the disclosed approach, it should greatly speed up the computation time of ultrasound images based on FWI, and also allows for more ultrasound data to be included in the image inversion, leading to much better image quality. This use could be applied, for example, in a geoscience context. In another use for the disclosed approach, real data acquisition may be performed using source encoding, i.e., each transducer uses a specific source function in order to speed the data acquisition process. In other words, obtaining data could be done in a matter of seconds or less, instead of minutes currently.

An important feature of the disclosed approach relies on the crosstalk-free aspect of the source encoding method. Thanks to this, the disclosed encoding provides exactly the same result as conventional inversion, but using two wave simulations per iteration, instead of 2*S simulations per iteration, where S represents the number of sources that are considered for inversion. This greatly increases the speed with which inversions (image reconstructions) can be conducted. Existing source encoding methods introduce artifacts that reveal to be of major negative impact when the number of sources increases. Therefore, the disclosed method allows for the reconstruction of higher quality images.

An exemplary application of the disclosed approach is a program that implements source encoding to speed up the computational process. Another exemplary application is an ultrasound device, with transducers simultaneously firing multiple, specific frequencies, instead of a more conventional one by one firing strategy. This greatly speeds up the data acquisition process.

The disclosed approach may be employed to construct a 3D ultrasound FWI scanner that provides accurate images in an acceptable time (<30 min). Other solutions would increase errors in the resulting images, because of 1) fewer sources recorded, 2) simplified physics in the inversion process, and 3) patient movement during scanning leading to blurring.

The disclosed method is implemented in two complementary ways. In the first approach, the encoded forward and adjoint wavefields are run until they reach a steady state, at which point they are "deblended" to obtain their stationary parts: one pair associated with each source in the dataset. The stationary parts of the encoded forward and adjoint wavefields are combined to calculate the misfit gradient by summing their respective contributions. In the second approach, the steady-state encoded forward and adjoint wavefields are convolved over a time period proportional to the inverse of the frequency bandwidth of interest. Using this strategy, the encoded forward and adjoint wavefields do not need to be deblended, nor is there a need to calculate or store intermediary stationary contributions to the gradient. A wide variety of source-encoded cost functions are considered, including waveform differences, phase and amplitude measurements, "double-difference" phase and amplitude measurements, cross-correlation travel-time measurements, or a generic adjoint tomography cost function. "Super measurements" are used based on source-encoded Fourier coefficients of entire observed and simulated seismograms, as in pure FWI, one iteration requires just two numerical simulations, independent of the number of sources and receivers. In terms of device development, the disclosed device will allow a significant speed-up of acquisition of data from equipment. For example, instead of taking measurements source by source, measurements can be taken across all sources simultaneously, rapidly decreasing the amount of time it takes to acquire ultrasonic data from an object, patient etc.

Accordingly, in one aspect, this disclosure provides a system for ultrasound tomography. The system may include: a plurality of sources configured to transmit waves at one or more frequencies within a frequency bandwidth; one or more receivers configured to receive the waves transmitted by the plurality of sources; and a processor configured to: (a) use a computerized representation of physical property maps of a medium that influence wave propagation; (b) model all the sources and the receivers involved in a dataset; (c) associate to each of the sources a sinusoidal source time function with a defined frequency of a set of frequencies regularly spaced within a bandwidth of interest; and (d) perform a wave propagation simulation where sources are transmitting simultaneously for a time $T_{ss}+k\Delta\Sigma$, where $T_{ss}$ is a simulation duration for simulated wavefield to reach a steady state, k is an integer$>=1$, and $\Delta_\tau=1/\Delta f$.

In some embodiments, the system may further include an ultrasound wave generator configured to associate each of the sources with a defined frequency $f_s$ of a set of frequencies regularly spaced at $\Delta f$ within a $[f_{min}, f_{max}]$ bandwidth.

In some embodiments, the processor may be further configured to: (e) receive observed measurements from at least one sensor based on a wave transmitted from at least one source passing through a medium; (f) estimate a frequency-domain observed pressure $\hat{p}_{obs}(x, f_s)$ for each source, where x is a spatial location of a receiver, $f_s$ is a frequency associated with source; (g) evaluate $$\hat{p}_{syn}(x, f_s) = \frac{1}{k\Delta\tau}\int_{T_{ss}}^{T_{ss}+k\Delta\tau} P_{syn}(x, t)e^{-2i\pi f_s(t-T_{ss})}$$

simultaneously for all sources at all receiver positions, where t is time of simulation; and (h) estimate a cost function based on the values of $\hat{p}_{obs}$ and $\hat{p}_{syn}$.

In some embodiments, the processor may be further configured to: (i) evaluate the gradient of the cost function for the bulk modulus κ, as defined by $$K_\kappa(x) = -\frac{2}{\Delta\tau}\int_{T_{ss}}^{T_{ss}+\Delta\tau} \kappa^{-1}(x)\partial_{t^2} P_{syn}^\dagger(x, T_{ss}+\Delta\tau-t)P_{syn}(x, t)dt,$$

where $P_{syn}^\dagger$ is an adjoint wavefield, and $\partial_{t_2}$ is a second order partial derivative in time, operator.

In some embodiments, the processor may be further configured to repeat steps (d) and (g)-(i) to minimize the cost function.

In some embodiments, the defined frequency $f_s=f_{min}+(s-1)\Delta f$ and $$\Delta f = \frac{f_{max}-f_{min}}{S-1},$$

where s denotes an individual source and S is the total number of sources, $f_s$ is frequency associated with source s, and $[f_{min}, f_{max}]$ is the bandwidth of interest.

In some embodiments, each source can be detected by a different subset of sensors. In some embodiments, the wave transmitted from the sources can be visco-acoustic waves.

In some embodiments, the simulation may include at least one forward simulation and adjoint simulation per iteration.

In some embodiments, the processor may be further configured to evaluate $$\widetilde{p_{syn}}(x_r, f_s; \tau) = \frac{1}{\Delta\tau}\int_{\tau}^{\tau+\Delta\tau} P_{syn}(x_r, t)e^{-2i\pi f_s(t-\tau)}dt$$

$\forall \{s, r\}, \forall \epsilon, \exists T_{ss}$ such that $\forall \tau > T_{ss}$:

$$|\widetilde{p_{syn}}(x_r, f_s; \tau) - \widetilde{p_{syn}}(x_r, f_s; T_{ss})| < \epsilon$$

where s represents a given source simulated in simulation, r represents a given receiver, that records a given source s, $x_r$ is the position of the receiver r, t is time of the simulation, $\tau$ is time after $T_{ss}$, Psyn is a wavefield simulated by a solver, $f_s$ is a frequency associated with source s, and $\epsilon$ can be any value.

In some embodiments, wherein the processor may be further configured to compute a gradient of the cost function represented by:

$$\chi w(m) = \frac{1}{2}\sum_{s=1}^{S}\sum_{r=1}^{R_s}|\widetilde{P_{syn}}(x_r, f_s; m) - \widetilde{P_{obs}}(x_r, f_s)|^2$$

where m is a wavespeed, density, attenuation map, or a combination, $\overline{P_{syn}}$ is the Fourier transform of the wavefield $P_{syn}$, and $\overline{P_{obs}}$ is the Fourier transform of the observed wavefield $P_{obs}$.

In some embodiments, the costfunction may include a source-encoded cost function that integrates contributions from all the sources. In some embodiments, the cost function comprises waveform differences, phase and amplitude measurements, double-difference phase and amplitude measurements, cross-correlation traveltime measurements, or a generic adjoint tomography cost function.

In some embodiments, the system may include an ultrasound device. In some embodiments, the medium comprises human tissue or soil. In some embodiments, the processor is further configured to generate an image representation of the medium.

In another aspect, this disclosure further provides a method for ultrasound tomography. The method may include: (i) using a computerized representation of physical property maps of a medium that influence wave propagation; (ii) modeling all the sources and the receivers involved in a dataset; (iii) associating to each of the sources a sinusoidal source time function with a defined frequency of a set of frequencies regularly spaced within a bandwidth of interest; and (iv) performing a wave propagation simulation where sources are transmitting simultaneously for a time $T_{ss}+k\Delta\tau$, where $T_{ss}$ is a simulation duration for simulated wavefield to reach a steady state, k is an integer>=1, and $\Delta_\tau=1/\Delta f$.

In some embodiments, the method may further include associating each of the sources with a defined frequency $f_s$ of a set of frequencies regularly spaced at $\Delta f$ within a $[f_{min}, f_{max}]$ bandwidth.

In some embodiments, the method may further include: (v) receiving observed measurements from at least one sensor based on a wave transmitted from at least one source passing through a medium; (vi) estimating a frequency-domain observed pressure $\hat{P}_{obs}(x, f_s)$ for each source, where x is a spatial location of a receiver, $f_s$ is a frequency associated with source s; (vii) evaluating $$\hat{p}_{syn}(x, f_s) = \frac{1}{k\Delta\tau}\int_{T_{ss}}^{T_{ss}+k\Delta\tau} P_{syn}(x, t)e^{-2i\pi f_s(t-T_{ss})}$$

simultaneously for all sources at all receiver positions, where t is time of simulation; and (viii) estimating a cost function based on the values of $\hat{P}_{obs}$ and $\hat{p}_{syn}$.

In some embodiments, the method may further include: (ix) evaluating the gradient of the cost function for the bulk modulus $\kappa$ as defined by $$K_\kappa(x) = -\frac{2}{\Delta\tau}\int_{T_{SS}}^{T_{SS}+\Delta\tau}\kappa^{-1}(x)\partial_{t^2}P_{syn}^\dagger(x, T_{SS}+\Delta\tau-t)P_{syn}(x, t)dt,$$

where $P_{syn}^\dagger$ is an encoded adjoint wavefield, and $\partial_{t_2}$ is a second order partial derivative in time, operator.

In some embodiments, the method may further include repeating steps (iv) and (vii)-(ix) to minimize the cost function.

In some embodiments, the defined frequency $f_s = f_{min}+(s-1)\Delta f$ and $$\Delta f = \frac{f_{max}-f_{min}}{S-1},$$

where s denotes an individual source and S is the total number of sources, $f_s$ is frequency associated with source s, and $[f_{min}, f_{max}]$ is the bandwidth of interest.

In some embodiments, each source can be detected by a different subset of sensors. In some embodiments, the wave transmitted from the sources may be visco-acoustic waves.

In some embodiments, the simulation may include at least one forward simulation and adjoint simulation per iteration.

In some embodiments, the method may further include evacuating $$\widetilde{p_{syn}}(x_r, f_s; \tau) = \frac{1}{\Delta\tau}\int_{\tau}^{\tau+\Delta\tau}P_{syn}(x_r, t)e^{-2i\pi f_s(t-\tau)}dt$$

$\forall \{s, r\}, \forall \epsilon, \exists T_{ss}$ such that $\forall \tau > T_{ss}$: $|\widetilde{p_{syn}}(x_r, f_s; \tau) - \widetilde{p_{syn}}(x_r, f_s; T_{ss})| < \epsilon$ where s represents a given source simulated in simulation, r represents a given receiver, that records a given source s, $x_r$ is the position of the receiver r, t is time of the simulation, $\tau$ is time after $T_{ss}$, Psyn is a wavefield simulated by a solver, $f_s$ is a frequency associated with source s, and $\epsilon$ can be any value.

In some embodiments, the method may further include computing a gradient of the cost function represented by:

$$\chi_1(m) = \frac{1}{2}\sum_{s=1}^{S}\sum_{r=1}^{R_s}\int_0^T \|p_{syn}(x_{s,r}, t, m) - p_{obs}(x_{s,r}, t)\|^2 dt$$

where m is a wavespeed, density, attenuation map, or a combination, $\overline{P_{syn}}$ is the Fourier transform of the wavefield $P_{syn}$, and $\overline{P_{obs}}$ is the Fourier transform of the observed wavefield $P_{obs}$.

The following sections describe in greater detail the disclosed methods and systems as well as their applications (e.g., ultrasound, earthquake seismology).

I. Source Encoding for Viscoacoustic Ultrasound Computed Tomography

Ultrasound computed tomography (USCT) is a noninvasive imaging modality that has shown its clinical relevance for breast cancer diagnostics. As opposed to traveltime inversions, waveform-based inversions can exploit the full content of ultrasound data, thereby providing increased resolution. However, this is only feasible when modeling the full physics of wave propagation, accounting for 3D effects such as refraction and diffraction, and this comes at a significant computational cost. To mitigate this cost, a cross-talk-free source encoding method for explicit time-domain solvers is disclosed herein, as shown in FIG. 1B. The gradient computation is performed with only two numerical "super" wave simulations, independent of the number of sources and receivers. The absence of crosstalk is achieved by considering orthogonal frequencies attributed to each source. By considering "double-difference" measurements, no a priori knowledge of the source time function is required. With this method, full-physics-based 3D waveform inversions can be performed within minutes using reasonable computational resources, fitting clinical requirements.

This disclosure presents a crosstalk-free source encoding technique for explicit solvers in USCT. In the context of waveform inversion, this method takes advantage of the computational efficiency and minimal memory requirements of an explicit solver, while only two wave simulations are used to compute the misfit gradient, regardless of the number of sources and receivers. This disclosure provides the equations for acoustic and viscoacoustic problems and illustrates the approach with different configurations, including synthetic and real data experiments. Computational considerations are emphasized to highlight the relevance and practical advantages of the disclosed technique.

i. Frequency-Domain Measurements

Due to the nature of the wave equation, the observed Green function, $G_{obs}(X, Xs, t)$, capturing wave propagation from a source $X_s$ to a position X, can be seen as a linear filter. It has a finite impulse response due to geometrical divergence and/or attenuation effects; its duration is denoted by $T_1$. In the time domain, one may express the observed pressure $p_{obs}(X, t)$ as a convolution of the observed Green function and the observed source time function, $S_{obs}(Xs, t)$, that is, $$P_{obs}(X,t) = \int_0^{T1} G_{obs}(x,x_s,t-\tau) S_{obs}(x_s,\tau) d\tau. \quad (1)$$

Let $T_2$ denote the duration of the source $s_{obs}$. It is assumed that the pressure time series is recorded over a duration $T \geq T_1 + T_2$, and the Fourier transform is applied:

$$\overline{P_{obs}}(x,f) = \int_0^T P_{obs}(x,t) e^{-2i\pi ft} dt \quad (2)$$

In the frequency domain, the observed pressure $p_{obs}(x, f)$ can be conveniently described as a product:

$$\overline{p_{obs}}(x,f) = G_{obs}(x,x_s,f) S_{obs}(x_s,f). \quad (3)$$

where $S_{obs}(Xs, f)$ denotes the observed source time function at frequency $f$ and $G_{obs}(X, Xs, f)$ the Green function of the medium between source $X_s$ and position X at frequency $f$.

Because the Green function $G_{obs}$ is directly influenced by the mechanical properties of the medium (e.g., sound speed, attenuation.), the frequency-domain observed pressure $\overline{P_{obs}}$ constitutes a relevant measurement in the context of waveform inversion. It is also compatible with the disclosed source encoding method, as shown in the next section.

ii. Source Encoding

In this section, how each source is encoded in a single numerical simulation and how to decode each source contribution from this "super" wave-field are illustrated. The advantages of the disclosed method were analyzed from a computational perspective.

A. Theory

1. Encoding

The key idea is to take advantage of the fact that for any $\Delta\tau$-periodic trigonometric polynomial $$P(t) = \sum_{n=-\infty}^{+\infty} c_n e^{2i\pi nt/\Delta\tau}. \quad (4)$$

its Fourier coefficients $c_n$ may be extracted based on the following expression:

$$c_n = \frac{1}{\Delta\tau} \int_0^{\Delta\tau} P(t) e^{-2i\pi nt/\Delta\tau} dt. \quad (5)$$

Numerically, it is possible to generate a wavefield behaving as an $\Delta\tau$-periodic trigonometric polynomial in any point of the domain by enforcing multiple monochromatic sources with regularly spaced frequencies. Rather than modeling the full spectrum of a certain source, one (or a few) specific frequencies, which are a multiple of $1/\Delta\tau$ are attributed.

Let us consider a set of S sources operating in the frequency band $[f_{min}, f_{max}]$. Each source s is associated with a monochromatic source time function with a frequency $$f_s = f_{min} + \frac{s-1}{\Delta\tau} \quad (6)$$

where $$\Delta\tau = \frac{S-1}{f_{max} - f_{min}} \quad (7)$$

Each source s, located at $X_s$ and transmitting at frequency $f_s$, may have a certain amplitude and phase shift, represented by a complex constant $S_{syn}(X_s, f_s)$, which can be useful to model a source time function. As for Eq. (3), the simulated pressure $p_{syn}$ of a single source in the medium may be expressed as follows:

$$\overline{P_{syn}}(x,f_s) = G_{syn}(x,X_s,f_s) S_{syn}(x_s,f_s). \quad (8)$$

where $G_{syn}$ denotes the synthetic Green function capturing monochromatic behavior at frequency $f_s$ due to a source located at $X_s$ recorded at position X.

Because an explicit time-domain solver is used, there are causality effects. To attain monochromatic behavior, the simulation must run sufficiently long to eliminate transient behavior of the wavefield, as illustrated in FIG. 3. $T_{ss}$ is used to denote the time required to reach this steady state.

When simultaneously firing multiple sources, after reaching a steady state, the resulting "super" wavefield may be expressed in the form $$\forall t \geq T_{ss}, P_{syn}(x,t) = R\sum_{s=1}^{S} p_{syn}(x,f_s) e^{2i\pi f_s t} \quad (9)$$

For any position X, $P_{syn}$ is a trigonometric polynomial of the form of Eq. (4) with a period determined by Eq. (7).

2. Decoding

An explicit time-domain solver is used to recover the individual synthetic pressures, $\widehat{p_{syn}}(x, f_s)$, embedded in Eq. (9). Once a steady state has been reached at time $T_{ss}$, Eq. (9) holds true, and the simulation must be run for an extra duration of $\Delta\tau$ seconds. Then, it yields $$\widehat{p_{syn}}(x, f_s) = \frac{1}{\Delta\tau} \int_{T_{ss}}^{T_{ss}+\Delta\tau} P_{syn}(x, t) e^{-2i\pi f_s(\tau - T_{ss})} dt \quad (10)$$

Figure 5A:
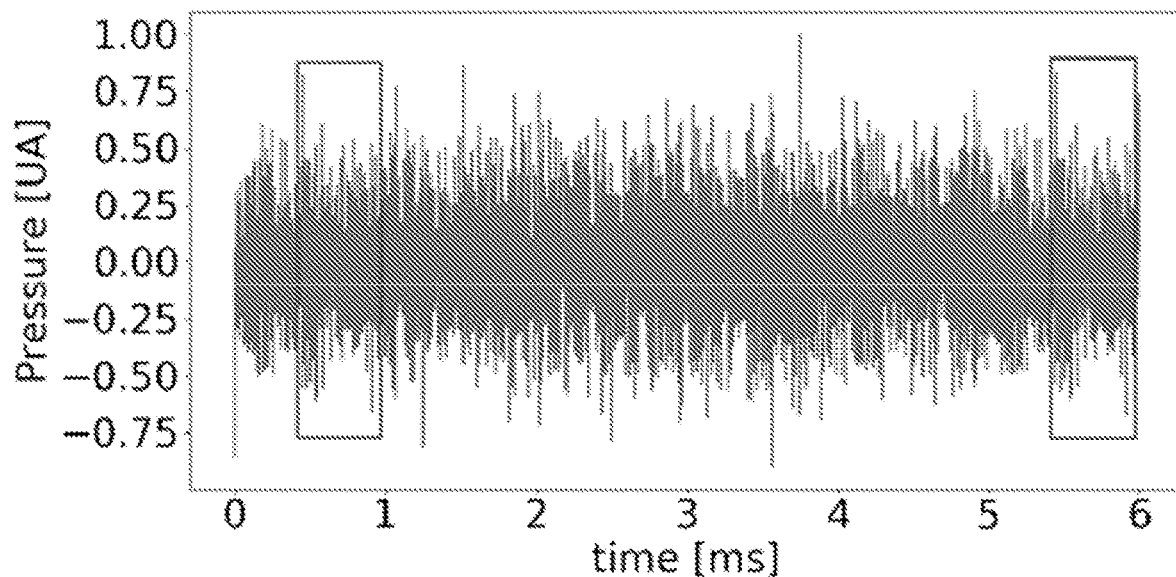
FIG. 5A shows typical data recorded in an encoded "super" simulation (Simulation C). After approximately 0.5 ms of the transient state. The data can be described by a trigonometric polynomial composed of 1,024 sinusoids for a duration of 5 ms. Within the two red boxes, it was observed that the signal repeats itself.
Figure 5B:
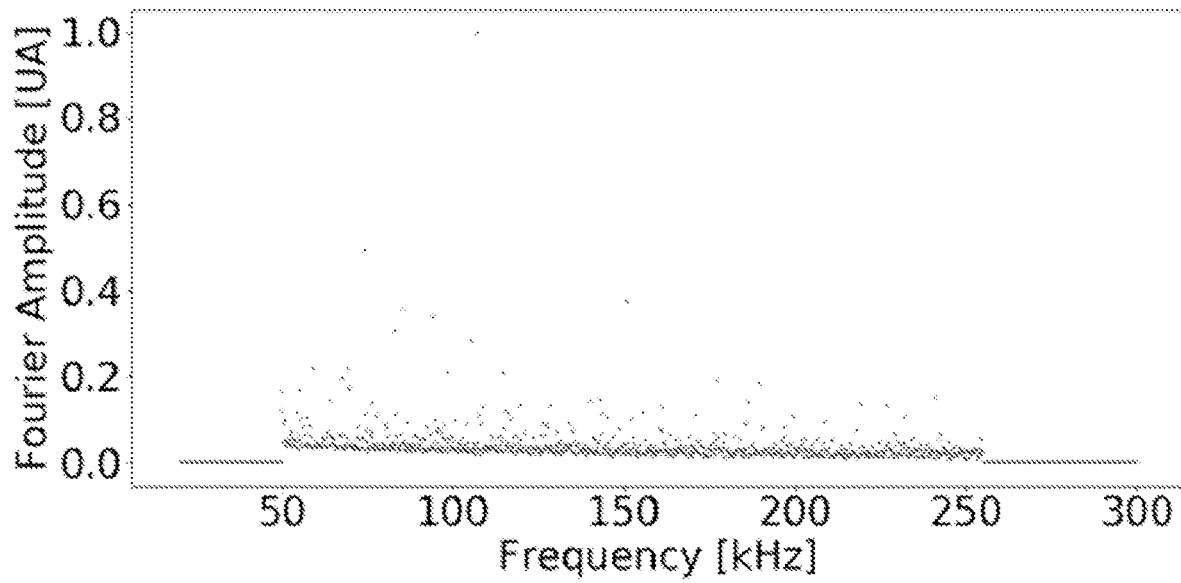
FIG. 5B shows the amplitude of data Fourier coefficients shown in FIG. 5A. Each point represents the Green function amplitude for each of the 1,024 sources, evaluated at specific frequencies according to Eq. (6). They may be computed using a fast Fourier transform over the last 5 ms window of the recorded data.

While $P_{syn}$ is a superposition of multiple monochromatic waves, Eq. (10) enables us to "decode" the contribution of each source without crosstalk thanks to the orthogonality of the Fourier basis, as illustrated in FIGS. 4 and 5, and discussed in more detail in Appendix B. Evaluation of Eq. (10) may be performed simultaneously for all sources using a fast Fourier transform, followed by a multiplication with $\exp(-2i\pi f_s T_{ss})$, which is equivalent to applying the delay theorem with a delay of $T_{ss}$ seconds.

It is worth noting that, contrary to the approach of (Capdeville et al., 2005; Geophys. J. Int. 162, 541-554), one may consider a different set of receivers for each source. Furthermore, if the same receivers are used, it is possible to discard some receivers for each source. For instance, when evaluating Eq. (10) through a fast Fourier transform, Fourier coefficients of frequencies that are not of interest may be discarded.

B. Practical Considerations

It may be a challenge to determine the time to reach a steady state, $T_{ss}$. Setting a very large value to ensure that transient effects have vanished can be time-consuming. For the breast model shown in FIG. 2, where the region of interest is surrounded by recording transducers, $T_{ss}$ may be deduced from the observed data. In FIG. 3D, there is no significant wiggle in the data after 0.25 ms, which suggests a choice of $T_{ss}$=0.25 ms. Because low frequencies may not appear in the data but involve longer periods, an extra duration equaling the period of the minimum frequency encoded may be added to $T_{ss}$. An alternative method is to numerically evaluate the following:

$$\widehat{p_{syn}}(x_r, f_s; \tau) = \frac{1}{\Delta\tau} \int_{\tau}^{\tau+\Delta\tau} P_{syn}(x_r, t) e^{-2i\pi f_s(t-\tau)} dt \quad (11)$$

$\forall \{s, r\}, \forall \epsilon, \exists T_{ss}$ such that $\forall \tau > T_{ss}$: $|\widehat{p_{syn}}(x_r, f_s; \tau) -$ $\widehat{p_{syn}}(x_r, f_s; T_{ss})| < \epsilon$ where s represents a given source simulated in simulation, r represents a given receiver, that records a given source s, $x_r$ is the position of the receiver r, t is time of the simulation, $\tau$ is time after $T_{ss}$, $P_{syn}$ is a wavefield simulated by a solver, $f_s$ is a frequency associated with source s, and $\epsilon$ can be any value.

While this approach is more accurate, evaluating Eq. (11) for multiple time windows, multiple frequencies, and multiple points can also be computationally expensive.

It is worth noting that while a single simulation suffices to encode as many sources as desired, the associated compute time still depends on the number of sources, since, according to Eq. (7), there is a linear dependence between the integration period $\Delta\tau$ and the number of sources S. When $T_{ss}$ is much smaller than $\Delta\tau$, the link between the number of sources and compute time becomes nearly linear. Nevertheless, a longer simulation with an explicit solver does not impose extra RAM requirements. Recorded data can be regularly written on disk during the simulation, or the decoded Fourier coefficients can be computed on the fly to avoid I/O. In addition, the overall compute time between one encoded simulation and S non-encoded simulations still significantly decreases. As shown in the next section, while small meshes can result in a speedup of around 50, larger meshes can result in a larger speedup, which can be in the thousands because of the increase in bandwidth. For instance, the expected speedup for a [500-1,500] kHz bandwidth is 10 times bigger than for a [50-150] kHz bandwidth, even though the ratio $f_{max}/f_{min}$ is the same for each case.

iii. Gradient Computation

In the context of waveform inversion, source encoding is used to compute the gradient of a cost function that integrates the contributions from all the sources, using only two "super" simulations.

A. Cost Function

To take full advantage of the disclosed source encoding method, frequency-domain measurements is considered. While time-domain data processing cannot be performed, the measurement computation requires just a single "super" simulation.

As an example, the classical waveform cost function is first considered $$\chi_W(m) = \frac{1}{2} \sum_{s=1}^{S} \sum_{r=1}^{R_s} \left| \widehat{p_{syn}}(x_r, f_s; m) - \widehat{p_{obs}}(x_r, f_s) \right|^2 \quad (12)$$

where m is a wavespeed, density, attenuation map, or a combination, $\overline{P_{syn}}$ is the Fourier transform of the wavefield $P_{syn}$, and $\overline{P_{obs}}$ is the Fourier transform of the observed wavefield $P_{obs}$.

While observed measurements $\overline{p_{obs}}$ may be determined using Eq. (2), these measurements are obtained for any frequency at a minimal computational cost is further described below. As discussed in the previous section, synthetic measurements $\overline{P_{syn}}$ may be obtained using Eq. (10).

In the frequency domain, observed and synthetic measurements can be interpreted as a product between a source time function and a Green function, as expressed in Eqns. (3) and (8). Thus, based on Eq. (12), matching the observed and synthetic Green functions was attempted. A challenge with this approach is that is predicated on the assumption that $$S_{syn}(x_s, f_s) \approx S_{obs}(x_s, f_s) \quad (13)$$

Alternatively, the observed source time function needs to be estimated from the data.

It is possible to avoid this challenge by considering the following "double difference" measurement:

$$\chi_Z^{DD} = \frac{1}{2} \sum_{s=1}^{S} \sum_{r=1}^{R_s} \sum_{r'>r}^{R_s} \left| \Delta\Delta\log Z_{rr'}^s \right|^2 \quad (14)$$

$$\Delta\Delta\log Z_{rr'}^s = \quad (15)$$

$$\log\left[\frac{\widehat{p_{obs}}(x_r, f_s)\widehat{p_{syn}}(x_{r'}, f_s)}{\widehat{p_{syn}}(x_r, f_s)\widehat{p_{obs}}(x_{r'}, f_s)}\right] = \log\left[\frac{G_{obs}(x_r, x_s, f_s)G_{syn}(x_{r'}, x_s, f_s)}{G_{syn}(x_r, x_s, f_s)G_{obs}(x_{r'}, x_s, f_s)}\right]$$

Contrary to the standard waveform cost function (12), this measurement does not depend on observed or synthetic source time functions. It only relies on matching observed and synthetic Green functions, which includes both phase and amplitude information, because the complex logarithm is defined as $$\log(z) = \ln|z| + i\mathrm{Arg}(z) \quad (16)$$

B. Adjoint Wavefield

The adjoint state method was used to determine Frechet derivative of the cost function. The adjoint wavefield is denoted by $P^\dagger(x, t)$. The adjoint source corresponding to the waveform cost function described in Eq. (12) is given by $$F^\dagger(x,t) = R\Sigma_{s=1}^{S}\Sigma_{r=1}^{Rs}[\overline{P_{syn}}(x_r, f_s; m) - \overline{P_{obs}}(x_r, f_s)] \times e^{2i\pi f_s t} \delta(x - x_r) \quad (7)$$

and the adjoint source corresponding to the double difference, complex logarithmic cost function (14) is given by $$F^{\dagger DD}{}_Z(x,t) = \Sigma_{s=1}^{S}\Sigma_{r=1}^{Rs}\Sigma_{r'\neq r}^{Rs}[R\{\Delta\Delta\log Z_{rr'}{}^s\}\cos(2\pi f_s t - \theta_{syn}) + \Im\{\Delta\Delta\log Z_{rr'}{}^s\}\sin(2\pi f_s t - \theta_{syn})]$$
$$A_{syn}{}^{-1}\delta(x - x_r) \quad (18)$$

where $\overline{P_{syn}} = A_{syn} \exp(-i\theta_{syn})$ with $A_{syn} \in \mathbb{R}^{+*}$ It is worth noting in Eqns. (17) and (18) that for each receiver r the adjoint source due to source s is a superposition of monochromatic sources of frequency $f_s$. Thus, by construction, the adjoint source involves for each source the same frequency content as the forward wavefield, and a single "super" adjoint wavefield suffices to compute the Frechet derivatives for all the sources.

To invert for attenuation, a second adjoint wave-field is computed to obtain the inverse bulk quality factor, $Q_\kappa^{-1}$, Frechet derivative. More details about modeling attenuation are provided in the sections below. This second adjoint wavefield uses a new adjoint source, based on a transformation of the adjoint source of Eqns. (17) or (18), namely, $$F^\dagger{}_{Q\kappa^{-1}}(x,t) = R\Sigma_{s=1}^{S}[(2/\pi)\ln(|f_s|/f_0) - i\mathrm{sgn}(f_s)] \times \overline{F^\dagger}(x, f_s)\exp(2\pi f_s t) \quad (19)$$

where $f_0$ is the frequency of reference for the bulk modulus.

C. Frechet Derivatives

The Frechet derivative expressions is adapted for acoustic media. The bulk modulus Frechet derivative, $K\kappa$, is taken as an example:

$$K_\kappa(x) \quad (20)$$

$$= -\frac{2}{\Delta\tau}\int_{T_{ss}}^{T_{ss}+\Delta\tau} \kappa^{-1}(x)\partial_{t^2} P^\dagger(x, T_{ss} + \Delta\tau - t)P(x, t)dt \quad (21)$$

$$= \Re \sum_{s=1}^{S} (2\pi f_s)^2 \kappa^{-1}(x)\vec{p}^{\dagger*}(x, f_s)\hat{p}(x, f_s) \quad (22)$$

It is interesting to note that the equalities Eqns. (21) and (22) are both of practical use, each with different advantages and disadvantages. Specifically, Eq. (22) requires decoding of both the "super" forward and the "super" adjoint wavefields using Eq. (10). To efficiently compute $\overline{p}^{\dagger*}(x, f_s)$ and $\hat{p}(x, f_s)$, one must hold these arrays in RAM memory for each point x and each frequency $f_s$, which is a significant cost. On the other hand, Eq. (21) does not require decoding the "super" wavefields, and the RAM memory needed to compute the Frechet derivative summed over all sources is similar to a standard forward wavefield run. The modest computational requirements facilitate streamlining the entire inversion workflow on a GPU, resulting in a reduction of I/O costs. Finally, the overall disk storage cost is greatly reduced because Frechet derivatives are summed on the fly.

Figure 2:
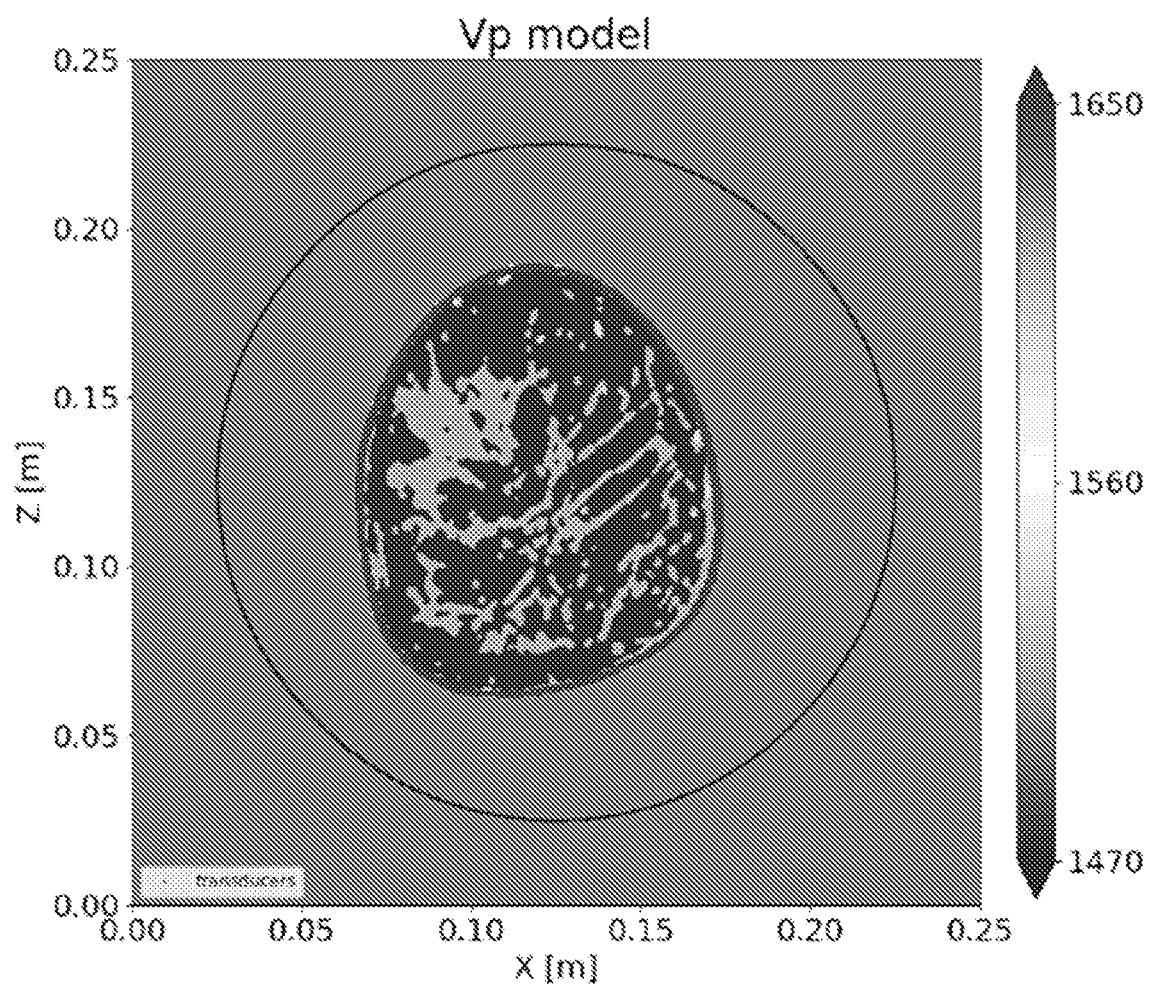
FIG. 2 is a diagram showing a model used to illustrate the method. This synthetic 2D compressional wavespeed (Vp) map of a breast immersed in water has been created using the extremely dense breast dataset (OA-Breast Database, dataset Neg 47 Left) from (Lou et al., 2017; Journal of Biomedical Optics 22). 1,024 transducers are placed around the breast, forming a circle with a 10 cm radius.

FIG. 6 illustrates the $K_\kappa$ Fréchet derivative computation with measurements from the model shown in FIG. 2. A complex logarithmic double difference cost function (Eq. (14)) and a homogeneous initial model are utilized. "Observed" data are obtained from 1,024 transient Ricker wavelet simulations (as in Simulation A). The two Frechet derivatives shown in column 1 are obtained from individual simulations of monochromatic sources (as in Simulation B), while column 2 uses simultaneously transmitting encoded sources (as in Simulation C). The minimal discrepancies displayed in column 3 prove the numerical feasibility of implementing Eqns. (21) and (22) for a large number of encoded sources.

iv. Synthetic Data Inversions

In this section, various numerical experiments are considered to illustrate the disclosed source encoding method and discuss strategies to maximize its benefits. All inversions are performed on a workstation with an Nvidia RTX 2080Ti GPU with 11 Gb of global memory, 16 Gb of RAM memory, 100 Gb of SSD NVMe memory, and 2Tb of HDD for data storage. As in the previous section, the SPECFEM2D and SPECFEM3D packages in single precision and the SeisFlows framework are used to perform inversions.

A. 2D Wavespeed Inversion

Figure 7A:
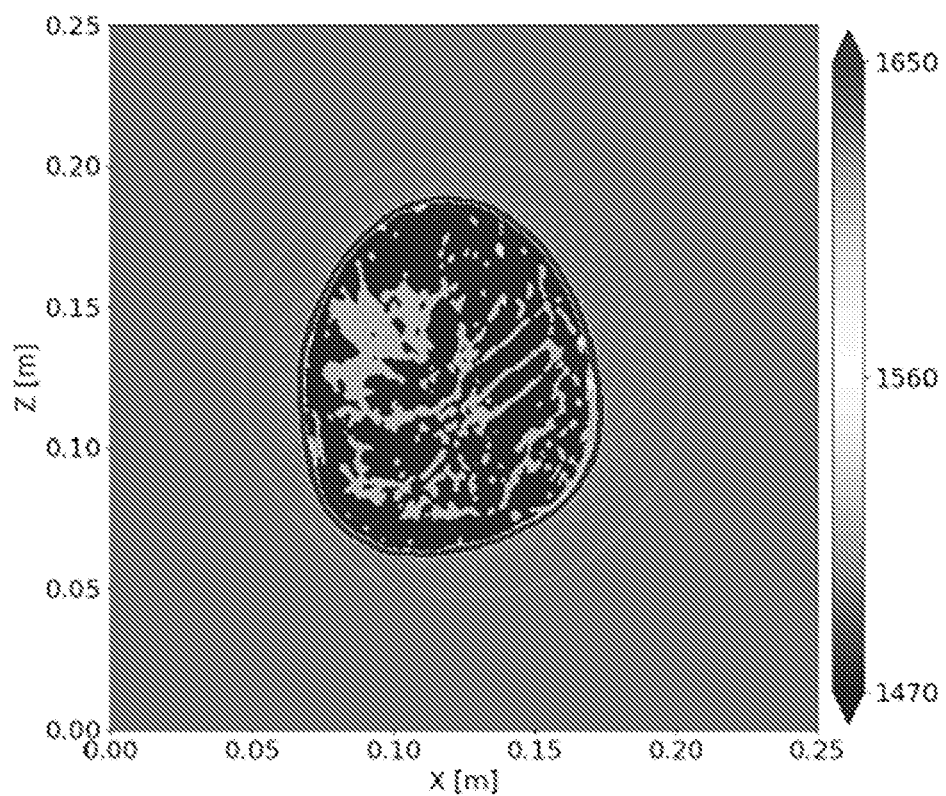
FIG. 7A shows the inverted result for the target model shown in FIG. 2. A progressive increase in frequency content with iterations mitigates cycle skipping.
Figure 7B:
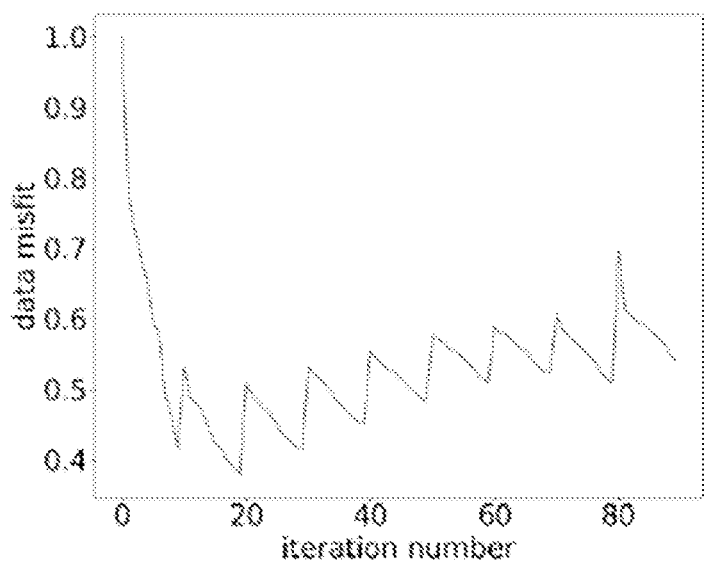
FIG. 7B shows evolution of the cost function as a function of iteration number. As shown, the cost function increases every 10 iterations due to a frequency increase of the measurements. Because of source encoding, this inversion was processed in 45 minutes on a single GPU. In a classical inversion, the same configuration would have required a month of computing time on the same hardware.
Figure 9:
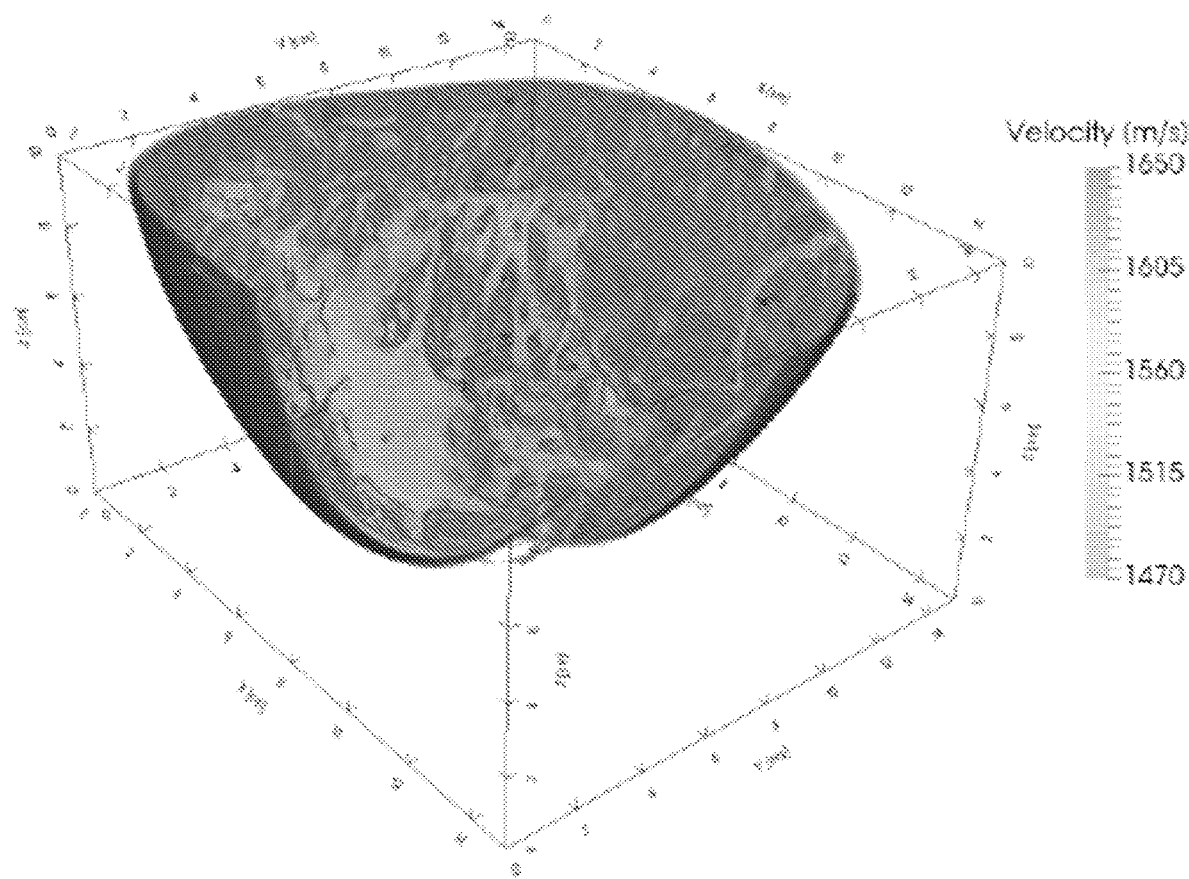
FIG. 9 shows a sliced view of the target wavespeed map for the 3D inversion example. Similar to FIG. 2, this breast model was created from data of (Lou et al., 2017; Journal of Biomedical Optics 22). 2,400 transducers are evenly spaced along four faces of the model. The 15 cm×15 cm×10 cm box is discretized using 281,250 spectral elements, each using 512 discretization points, enabling accurate simulations up to 1.1 MHz.

As a first example, the wavespeed model shown in FIG. 2 as a target map is used. As in FIG. 6, complex logarithmic double difference measurements and a homogeneous initial model are employed. "Observed" data are obtained for each source from five combined Ricker wavelet source time functions to cover a bandwidth from 50 kHz to 3 MHz. Because of the embedded phase measurement, cycle skipping may occur. To avoid this, measurements are made in the [50-450] kHz bandwidth for 10 iterations, then the bandwidth is increased by 25% and process 10 more iterations, and so on until the spectrum is covered up to 3 MHz. Proceeding this way, a coarse mesh is used at the beginning of the process, which properly models low frequencies while using minimal computational resources. When increasing the bandwidth, the mesh is updated accordingly and the previous wavespeed map is interpolated onto the new mesh. At each iteration, one million frequency-domain measurements are used, leading to rapid convergence, as shown in FIG. 7.

$T_{ss}$=0.25 ms of wave propagation were simulated, and $\Delta\tau \approx 2.56$ ms was used for the first ten iterations. Super simulations are 2.81 ms long while standard simulations are 0.25 ms long, but the gradient can be computed with only two super simulations, in contrast with 2,048 standard simulations in the usual case. The theoretical speedup is 91X. The practical speedup is even more important, because multiple solver initializations are avoided, in addition to significantly reduced I/O. When refining the mesh, the available bandwidth increases, and one can reduce the value of $\Delta\tau$. During the ten last iterations, $\Delta\tau$ 0.34 ms was used, leading to a 863× speedup compared to a standard inversion. Taking advantage of the increase in bandwidth helps to further reduce the impact of mesh refinement over compute time. This inversion, which involves 1,024 sources, 1,024 receivers, 90 iterations, and a data content up to 3 MHz, requires a compute time of 45 minutes using a single GPU.

B. 2D Joint Inversion

The same configuration was used as in the previous test—this time including attenuation effects-using the target attenuation map shown in FIG. 8A. The initial models of V, and $Q_K$ are homogeneous.

As shown in FIG. 8, despite crosstalk between $V_p$ and $Q_\kappa$ and low attenuation effects, global convergence is achieved for both maps. The cost function evolves in a similar fashion as in the pure $V_p$ inversion. As described previously, the $K_{Qk}-1$ Frechet derivative is obtained with a second adjoint wavefield computation. In terms of pute time, an iteration of a joint $Vp-Q_k^{-1}$ inversion is around two times slower than a $V_p$— only inversion. To compute the Frechet derivatives one must cross-correlate forward and adjoint wavefields. To avoid significant I/O transfers and storage costs of the forward wavefield, the forward wavefield was recompute on the fly during the adjoint wavefield computation. The approach of Komatitsch et al. (Komatitsch et al., 2016; Geophys. J. Int. 206(3), 1467-1478) was used to reconstruct the forward wavefield, as it eliminates any concerns with regards to numerical stability of the backward reconstruction of a wavefield when attenuation effects are incorporated.

C. 3D wavespeed inversion

The target map for the 3D example is a breast model constructed with the extremely dense breast dataset (OA-Breast Database, dataset Neg 47 Left) from (Lou et al., 2017; Journal of biomedical optics 22). 2,400 transducers evenly spaced on four faces of the model (600 transducers per face) were used, which act as sources and receivers. "Observed" data are simulated with 2,400 wave simulations, with each transducer emitting one-by-one a source time function combining two Ricker wavelets with 140 kHz and a 420 kHz central frequencies to cover the [50-1,100] kHz bandwidth. The map is modeled in a 15 cm×15 cm×10 cm domain, and discretized with 281,250 spectral elements, each using 512 discretization points. The local grid involves 144 million points, resulting in a 549 Mb wavespeed map. The corresponding SPECFEM3D run uses 5.3 Gb of RAM memory and 3.7 Gb of GPU global memory, which highlights the modest memory requirements of explicit solvers.

Figure 10:
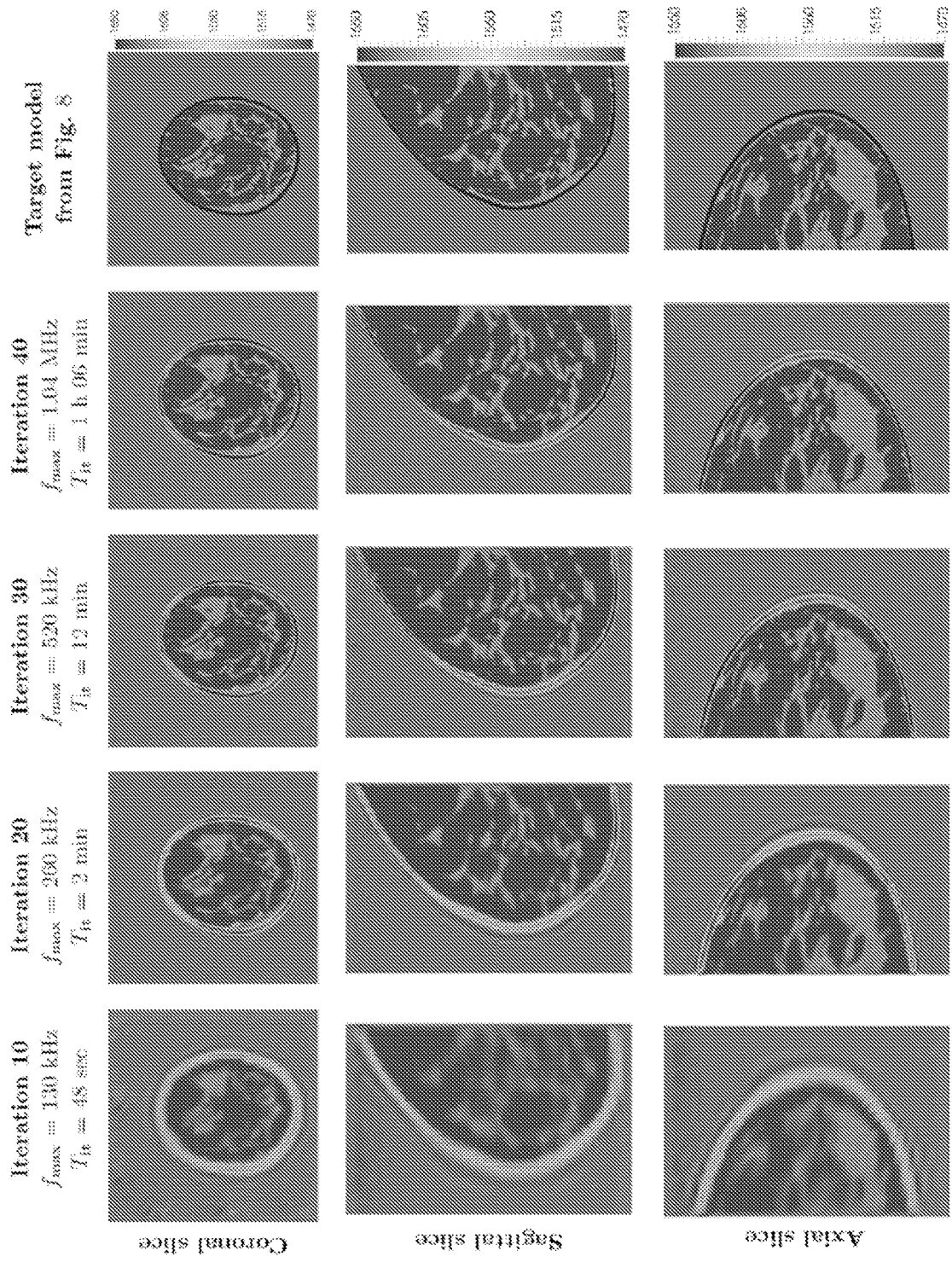
FIG. 10 shows 3D wavespeed inversion results of the target model presented in FIG. 9. Coronal, sagittal, and axial slices are taken at the middle of the model. Columns 1, 2, 3, and 4 present the inverted model at different iterations. The maximum inverted frequency $f_{max}$ is doubled every ten iterations. $T_{it}$ indicates the computing time used to perform one full iteration, involving 4 "super" simulations, for a model with a maximum modeled frequency $f_{max}$.

Inversion results are presented in FIG. 10. As for the 2D examples, the inversion is performed over different frequency ranges. The ten first iterations are performed in the [20-130] kHz range, followed by ten iterations on the [40-260] kHz range, then ten iterations in the [80-520] kHz range, and finally ten iterations in the [160-1,040] kHz range. As for the 2D case, the mesh was changed when changing the frequency range of interest to save computing time. Iteration 10 is reached after 8 minutes, iteration 20 is reached after 28 minutes, iteration 30 is reached after 2 hours and 26 minutes, and finally iteration 40 is reached after 15 hours and 30 minutes. It was observed that global convergence is ensured, while resolution increases when higher frequencies are assimilated. Between each bandwidth change, the maximum frequency was doubled. This requires doubling the number of integration points in each spatial dimension, while the CFL condition imposes a time step twice as small. Thus, for a similar simulated duration, the compute time is 16 longer when doubling the highest frequency. However, thanks to the disclosed source encoding method, it was observed that, when changing from the [80-520] kHz range to the [160-1,040] kHz range, the compute time is only 6.5 times longer.

Larger problems involving a bigger ROI or a higher frequency range can be handled using the multi-GPU capability of the SPECFEM3D package. Unlike implicit methods, this explicit solver achieves excellent weak and strong scaling.

v. Real Data Inversion

Figure 11A:
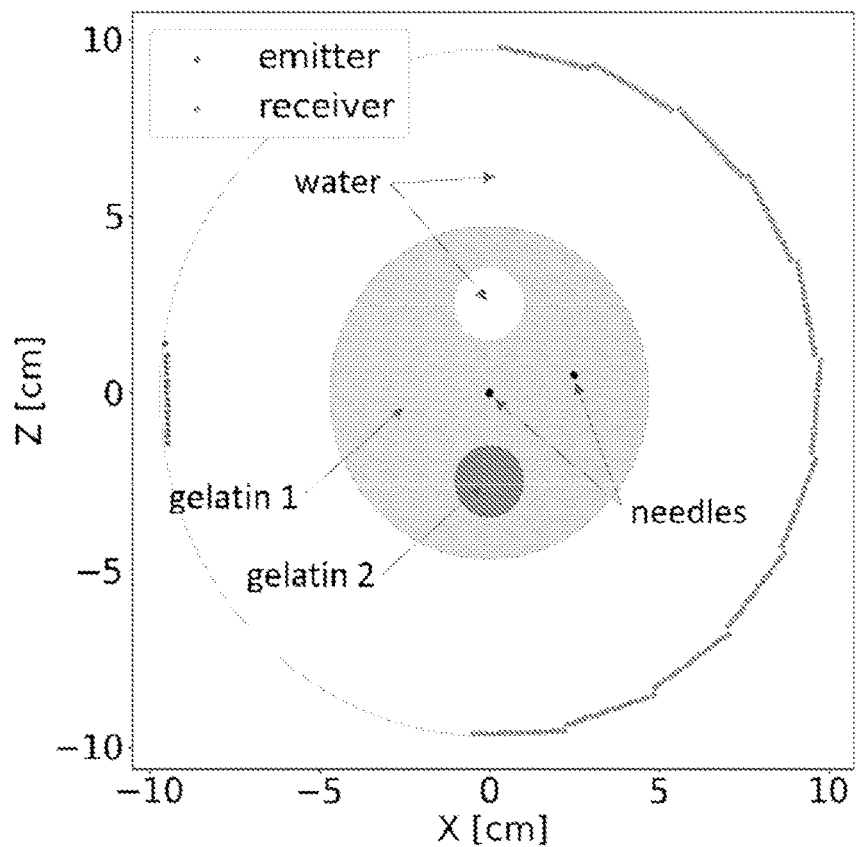
FIG. 11A shows an experimental configuration of the MUBI dataset (Camacho et al., 2012; Archives of Acoustics 37(3), 253-260). Each of the 16 emitters transmits one-by-one a wave recorded by 176 receivers. This experiment is repeated 23 times, rotating the emitter-receiver geometry along the blue circle.

In this example, the disclosed source encoding method was applied to the open-source Multimodal Ultrasound Breast Imaging System (MUBI) dataset for the SPIE USCT Data Challenge 2017 (Ruiter et al., 2017; International Society for Optics and Photonics, Vol. 10139, p. 101391N). The experimental setup consists of two linear transducer arrays with 16 active elements and a central frequency of 3.5 MHz. Each array can rotate around the region of interest, as described in FIG. 11A. One array emits element by element and one array records. Each transmission is repeated 11 times to record the wavefield at different positions by moving the recording array. Each ultrasound transmission is recorded at 11×16=176 different positions. This process is repeated 23 times, rotating the emitter and receiver arrays around the ROI. In total, 368 ultrasound transmissions are realized. The imaged object is a phantom composed of water, gelatine, graphite powder, alcohol, and two 0.25 mm diameter steel needles.

To obtain the synthetic measurements within a single super simulation, the synthetic pressure was recorded at all 176×23=4,048 positions that are used in the real experiment, even if a single transmission is recorded at only 176 different positions. When a source is not recorded by a given receiver, then—for this receiver dataset—the coefficient of the frequency associated with this source was discarded.

Figure 11B:
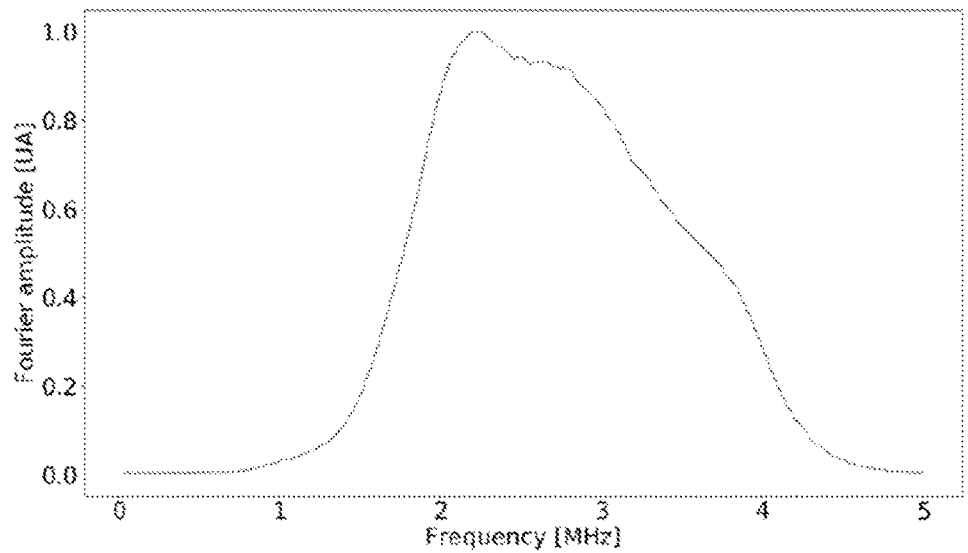
FIG. 11B shows typical Fourier amplitude of the recorded data, with most of the energy located in the [1-4.5] MHz range.

The initial model is homogeneous. A complex logarithmic double difference cost function was used, to avoid an estimation of the source time function, and "empty" measurements (measurements made in pure water) were not used in the analysis. The amplitude spectrum of the data is shown in FIG. 11B. The inversion is first performed in the [50-500] kHz bandwidth, despite a very weak signal for this frequency range, to avoid cycle skipping. The bandwidth is progressively enlarged to higher frequencies. Inversion results are presented in FIGS. 11C and 10D. Despite some cycle skipping artifacts, inherent to the lack of low frequency content, global convergence is obtained. Even with a minimum wavelength of 0.75 mm for assimilated data, in both images, the signature of the 0.25 mm needles is noticeable.

As the emitting and receiving transducer characteristics are not known, they are modeled as a point source/receiver, which largely reduces the expected resolution, in particular for a waveform-based measurement.

This point source modeling becomes less valid with increasing frequency and explains the weak resolution improvement between FIGS. 11C and 11D. Attempts to invert a frequency content higher than 2 MHz failed, as the point source approximation no longer holds.

vi. Additional Examples

A. Viscoacoustics and Constant-q Absorption Band Model

In the absence of attenuation, wave propagation may be represented by the following equation:

$$\kappa^{-1}\partial_t^2 p - \nabla \cdot (\rho^{-1} \nabla p) = 0 \tag{A1}$$

where $\kappa = \rho V_p^2$ denotes the bulk modulus, $\rho$ the mass density, $V_p$ the compression wavespeed, $f$ the source term, and $p$ the acoustic pressure. To incorporate effects due to attenuation using a constant-Q absorption band model, the bulk modulus becomes frequency-dependent, namely, $$\kappa(f) = \kappa(f_0)\left[1 + \frac{2}{\pi Q_\kappa} \ln\left(\frac{f}{f_0}\right)\right] \tag{A2}$$

where $f_0$ is a frequency of reference and $Q_\kappa$ the bulk quality factor. Alternatively, a power-law Q-model is readily accommodated. Thus, to describe attenuation, one must provide $Q_\kappa(x)$ and $\kappa(x, f_0)$ maps for a chosen frequency of reference f0. Modeling of an absorption band model using a time-domain solver can be achieved using a series of standard linear solids (SLS). Based on the experiments, three SLS are enough to properly model attenuation effects in a frequency band that is two decades wide. From a computational perspective, a viscoacoustic simulation is about 70% slower than a purely acoustic simulation and uses about 35% of additional RAM memory with the SPECFEM package.

B. Orthogonality

For s≠s', using Eq. (6), $$\frac{1}{T}\int_{t_0}^{t_0+T} \exp(-2\pi i f_{s'} t)\exp(2\pi i f_s t)dt = \quad (B1)$$

$$\frac{1}{T}\int_{t_0}^{t_0+T} \exp[2\pi i(s-s')t/\Delta\tau]dt =$$

$$\frac{1}{T}\frac{\exp[2\pi i(s-s')t_0/\Delta\tau]}{2\pi i(s-s')/\Delta\tau}\{\exp[2\pi i(s-s')T/\Delta\tau] - 1\}$$

Thus, as long as T=nΔτ, for some integer n, this yields $$\frac{1}{T}\int_{t_0}^{t_0+T} \exp(-2\pi i f_{s'} t)\exp(2\pi i f_s t)dt = \delta_{s's} \quad (B2)$$

This orthonormality of the Fourier basis is at the heart of the source encoding algorithm.

vii. Conclusions

This disclosure demonstrated the feasibility of a crosstalk-free source encoding method for explicit solvers in the context of medical imaging. This enables waveform inversion based on full-physics modeling. The approach is compatible with modest computational resources, because RAM memory requirements do not depend on the number of sources, despite all sources being simultaneously inverted. The disclosed approach scales linearly on thousands of, thereby providing an opportunity to further reduce the computational cost.

While the compute cost of a 3D explicit solver is proportional to the fourth power of the highest modeled frequency, the cost of a 3D inversion with the disclosed method is proportional to the third power of the highest modeled frequency. Even if some challenges remain at higher frequencies, this full-physics-based approach becomes more relevant as diffraction and other 3D effects become increasingly important, including in soft tissue. These improvements, combined with future generations of GPUs, help us anticipate the possibility of performing 2 MHz and higher inversions with 3D full physics for breast imaging using reasonable computational resources within the next decade.

II. Source Encoding for Adjoint Tomography and its Applications in Geoscience

A version of source encoding is used to facilitate the calculation of the gradient of a cost function independent of the number of sources or receivers. The crosstalk-free method requires only two numerical simulations per iteration, namely, one source-encoded forward simulation and one source-encoded adjoint simulation. Importantly for practical applications, each source does not need to be recorded by all receivers. The method is implemented in two complementary ways. In the first approach, the encoded forward and adjoint wavefields are run until they reach a steady state, at which point they are 'decoded' to obtain their stationary parts. These stationary parts are combined to calculate the misfit gradient by summing their respective contributions. In the second approach, the steady-state encoded forward and adjoint wavefields are convolved over a time period proportional to the inverse of the encoded frequency spacing. Using this strategy, the encoded forward and adjoint wavefields do not need to be decoded, nor is there a need to calculate or store intermediary stationary contributions to the gradient. A wide variety of source-encoded cost functions are considered, including waveform differences, phase and amplitude measurements, double-difference phase and amplitude measurements, cross-correlation traveltime measurements, or a generic adjoint tomography cost function. When measurements in specific time windows are involved in the construction of the source-encoded cost function, as in adjoint tomography, the computational cost scales linearly with the number of seismic sources, because the necessary synthetic seismograms must be computed individually. In contrast, when using super measurements' based on source-encoded Fourier coefficients of entire observed and simulated seismograms, as in pure full-waveform inversion (FWI), one iteration requires just two numerical simulations, independent of the number of sources and receivers. The method is illustrated based on examples from both earthquake and exploration seismology, highlighting inversion options and strategies involving frequency—and time-domain encoding, decoding (with more than 16 000 frequencies), encoded frequency randomization, encoding multiple frequencies per source, effects of noise, a variable number of receivers per event, various measurements and related cost functions and attenuation.

In this application, the following Fourier convention is used, $$s(x,\omega)=\int_{-\infty}^{\infty} s(x,t)\exp(-i\omega t)dt \quad (23)$$

with inverse $$s(x, t) = \frac{1}{2\pi}\int_{-\infty}^{\infty} s(x, \omega)\exp(i\omega t)d\omega \quad (24)$$

Here s denotes a vector displacement field, x a position vector, t time, and ω angular frequency.

i. Forward Wavefield in Earthquake Seismology, the Seismic Source May be Represented as an Equivalent Body force of the form:

$$f_j(x,t)=-M_{jk}(x_s)\nabla_k\delta(x-x_s)S(t) \quad (25)$$

where Mk denotes an element of centroid moment tensor, $x_s$ the centroid location, and S(t) the source time function. In terms of the Green's function, Gij(x, x', t–t'), the displacement field due to a body force may be expressed in the form:

$$s_i(x,t)=\int_{-\infty}^{t} Gij(x,x',t-t)f_j(x',t')d^3x'dt' \quad (26)$$

Written out explicitly, the displacement due to a point force (25) becomes $$s_i(x,t)=\int_{-\infty}^{t} \nabla_k Gij(x,x_s;t-t')M_{kj}(x_s)S(t')dt' \quad (27)$$

The goal will be to design a method for the calculation of Frechet derivatives that combines a set of earthquakes into a single distributed encoded 'super' source, thereby significantly reducing the numerical cost of an inversion.

ii. Source Encoding

To perform adjoint tomography with a set of S sources in an angular frequency band $[\omega_{min}, \omega_{max}]$. The goal is to perform such an inversion based on just a single combination of encoded 'super' forward and adjoint simulations by effectively tagging each individual source. This is accomplished by randomly assigning each source s a unique frequency, $\omega_s$, s=1, . . . , S, defined by $$\omega_s = \omega_{min} + (s-1)\Delta_\omega \qquad (28)$$

where $$\Delta\omega = (\omega_{max} - \omega_{min})(S-1) \qquad (29)$$

thereby covering the frequency band of interest, $[\omega min, \omega max]$.

The approach will be to run encoded forward and adjoint simulations driven by a superposition of monochromatic sources with frequencies (Eq. (28)) until the wavefields reach a steady state after some time $T_{ss}$. The technique will take advantage of the fact that the source-encoded Fourier basis is orthogonal in the following sense:

$$\frac{1}{\Delta\tau}\int_{T_{ss}}^{T_{ss}+\Delta\tau} \exp(-i\omega_s t)\exp(i\omega_{s'} t)dt = \delta_{ss'} \qquad (30)$$

where $$\Delta\tau = \frac{2\pi}{\Delta\omega} = \frac{2\pi(S-1)}{\omega_{max} - \omega_{min}} \qquad (31)$$

The time interval $\Delta\tau$ determines a period of integration required for 'deblending' or 'decoding' the encoded forward and adjoint wavefields, as well as the length of the convolution of the encoded forward and adjoint wavefields for the calculation of Frechet derivative.

While Huang & Schuster (2018) (Geophys. Prospect., 66, 1243-1257) and Dai et al. (2013) (Geophysics, 78, S233-S242) choose $T_{ss}=\Delta\tau$, this choice leads to poor performance when many frequencies are encoded, or to strong spectral leakage in the gradient when few frequencies are encoded. On one hand, as expressed in Eq. (31), $\Delta\tau$ solely depends on the available bandwidth and the number of encoded frequencies. On the other hand, $T_{ss}$ is determined by simulation parameters, such as wave speeds and the spatial dimensions of the domain. Intuitively, a steady state is obtained once transient effects disappear. Practically, one can compute the Fourier coefficients of the encoded wavefield evaluated at the encoded frequencies (28) over a time interval $[t_0; t_0+\Delta\tau]$. There exists a time $T_{ss}$ such that these coefficients remain unchanged for any $t_0 > T_{ss}$. This evaluation may be performed prior to inversion.

In practice, the set of frequencies determined by (28) is randomly distributed over the sources at the start of every iteration, and it was demonstrated that one may choose to assign more than one frequency per source. If the number of frequencies per source is $N_f$, then there are a total of $SN_f$ frequencies. In that case, the bandwidth of interest is divided up accordingly:

$$\Delta\omega = (\omega_{max} - \omega_{min})/(SN_f - 1) \qquad (32)$$

and the time interval for integration becomes $$\Delta\tau = \frac{2\pi}{\Delta\omega} = \frac{2\pi(SN_f - 1)}{\omega_{max} - \omega_{min}} \qquad (33)$$

iii. Encoding Forward Wavefield

To encode the forward wavefield, for a specific source s, Eq. (27) can be expressed in the frequency domain as $$S_i^s(x,\omega) = \nabla_k G_{ij}(X,x_s;\omega)M_{kj}(x_S)S_s(\omega) \qquad (34)$$

where $S_s$ denotes the source-time function associated with source s. At source frequency $\omega_s$, the stationary field is defined as $$s_i^s(x) \equiv s_i^s(x, \omega_s) = \nabla_k G_{ij}(x, x_s; \omega_s)M_{kj}(x_s)S_s(\omega_s) \qquad (35)$$

$$S_i(x, t) \equiv \Re \sum_{s=1}^{S} s_i^s(x)\exp(i\omega_s t) = \qquad (36)$$

$$\Re \Sigma_{s=1}^{S} \nabla_k G_{ij}(x, x_s; \omega_s)M_{kj}(x_s)S_s(\omega_s)\exp(i\omega_s t) =$$

$$\Re \Sigma_{s=1}^{S} M_{kj}(x_s)S_s(\omega_s)\int_{-\infty}^{\infty} \nabla_k G_{ij}(x, x_s; t')\exp(-i\omega_s t')dt' \exp(i\omega_s t)$$

$$= \Re \sum_{s=1}^{S} \int_{-\infty}^{\infty} \nabla_k G_{ij}(x, x_s; t - t')M_{kj}(x_s)S_s(\omega_s)\exp(i\omega_s t')dt'$$

Based on the results discussed in the above section about forward wavefield, the last equality motivates the definition of the encoded time-domain super source $$F_j(x,t) = R\Sigma_{s=1}^{S}(x,\omega_s)\exp(i\omega_s t) \qquad (37)$$

where $f_j^s(x, \omega_s)$ denotes the Fourier transform of body force (25) associated with sources. Effectively, all sources broadcast simultaneously, each at its own unique frequency $\omega_s$. Encoded super sources for an earthquake modeled by a Gaussian moment-rate tensor and a shot modeled by a Ricker wavelet are presented above.

The encoded super source (37) gives rise to the encoded forward wavefield $$S_i(x,t) = \int_{-\infty}^{t}\!\!\int G_{ij}(x,x';t-t')F_j(x',t')d^3x'dt' \qquad (38)$$

Thus the recipe for calculating the encoded super forward wavefield is simple: combine all earthquakes into the source-encoded super source (15) and run one forward simulation to obtain the encoded super forward wavefield (38).

iv. Decoding the Encoded Forward Wavefield

The encoded forward simulation (38) is carried out until the wavefield reaches a steady state at a time $T_{ss}$, that is, until it can be expressed as a trigonometric polynomial where $$S_i(x, t) = \Re \sum_{s=1}^{S} s_i^s(x)\exp(i\omega_s t) \qquad (39)$$

$$= \sum_{s=1}^{S} [A_i^s(x)\cos(\omega_s t) + B_i^s(x)\sin(\omega_s t)]$$

$$S_i^s = A_i^s(x) - iB_i^s(x) \qquad (40)$$

where $$A_i^s(x) = \Re s_i^s(x) \qquad (41)$$

and $$B_i^s(x) = -\Im s_i^s(x) \qquad (42)$$

Using the orthogonality relationship (30), the stationary parts of the encoded forward wavefield $S_i(x, t)$ may be 'deblended' or 'decoded' based on the following integrations:

$$A_i^s(x) = \frac{2}{\Delta\tau}\int_{T_{ss}}^{T_{ss}+\Delta\tau} S_i(x, t)\cos(\omega_s t)dt \qquad (43)$$

$$B_i^s(x) = \frac{2}{\Delta\tau}\int_{T_{ss}}^{T_{ss}+\Delta\tau} S_i(x, t)\sin(\omega_s t)dt \qquad (44)$$

The time $\Delta\tau$ required for decoding is defined by Eq. (31). Alternatively, the stationary parts may be determined based on trigonometric interpolation of the steady-state encoded forward wavefield using a nonuniform fast Fourier transform.

The Fourier coefficients of interest, $A_i^s(x)$ and $B_i^s(x)$, may also be obtained based on a discrete Fourier transform of the steady-state encoded forward wavefield (39). This is possible when the sampling frequency $\Delta f$ of the seismograms is chosen multiple of $1/\Delta f$, (2) the Shannon theorem is respected, that is $\Delta f > \omega_{max}/\pi$, and (3) $\omega_1 = \omega_{min}$ must be chosen as a multiple of $\Delta\omega$. Under these conditions, the vector generated by the fast Fourier transform has a subset that contains exactly the Fourier coefficients of the encoded frequencies $\omega_s$, $s=1, \ldots, S$. The delay theorem must be applied to recover the correct phase at $T_{ss}$.

v. Full Waveform Inversion

To develop intuition for inversions based on the encoded forward wavefield (38), the simple case of classical FWI is first considered.

A. Classical FWI

Figure 1B:
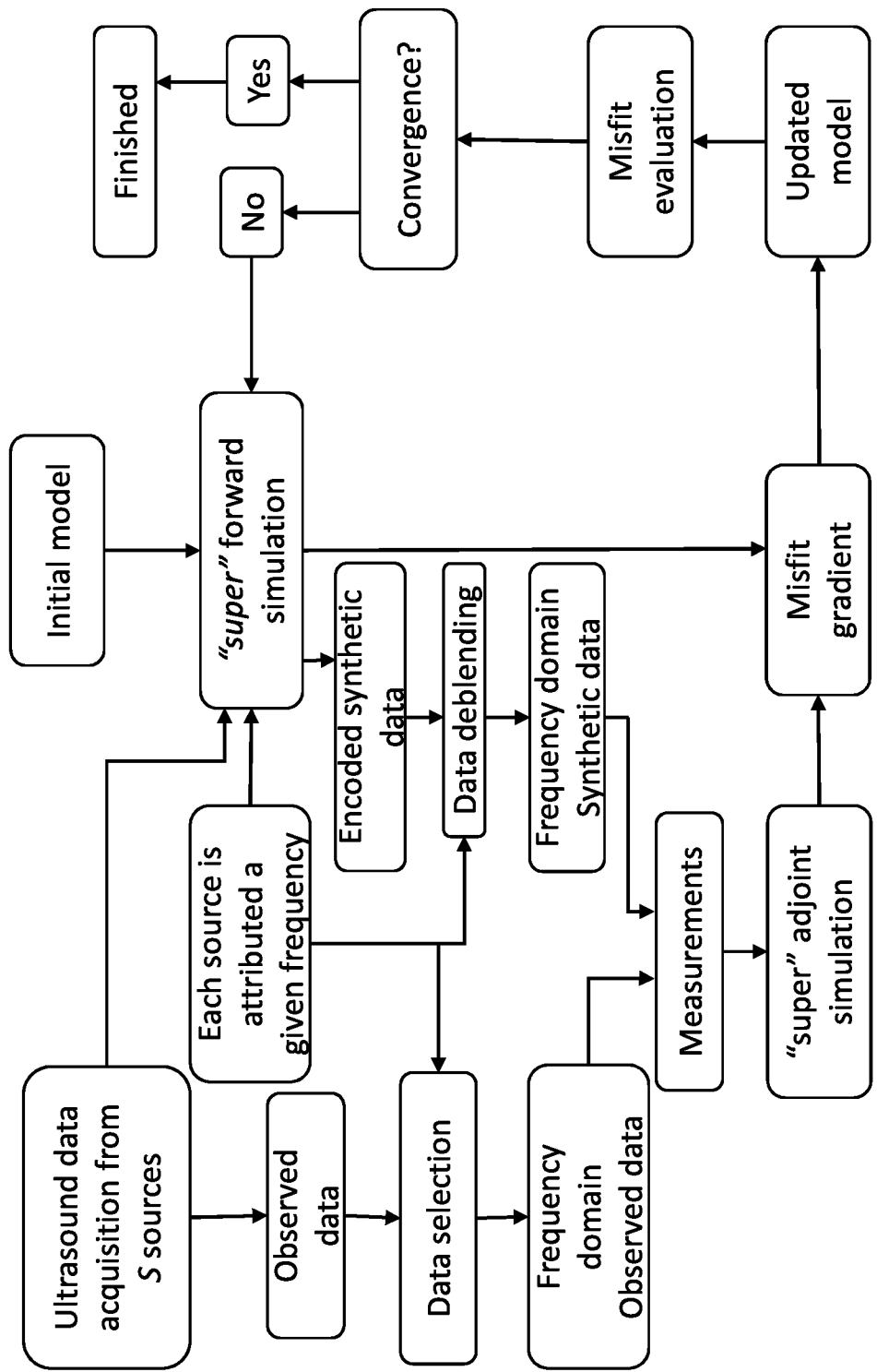
FIG. 1B shows a flowchart illustrating source encoded waveform inversion.

FIG. 1A is a flowchart illustrating a classical waveform inversion. For a given shot or sources, the classical FWI cost function is defined by (Tarantola 1984a, 1986)

$$\chi_s = \frac{1}{2}\sum_{r=1}^{R_s} \int [s_i^s(x_r, t) - d_i^s(x_r, t)]^2 dt \qquad (45)$$

Where $d_i^s(x_r, t)$ denote the data recorded at receiver r for sources, and where $r=1, \ldots, R_s$ labels the receivers that recorded events. It is important to recognize that in earthquake seismology, an event is typically recorded by a subset of the available receivers. The variation of the cost function (45) is $$\delta\chi_s = \Sigma_{r=1}^{R_s}\int[s_i^s(x_r,t)-d_i^s(x_r,t)]\delta s_i^s(x_r,t)dt \qquad (46)$$

and the associated adjoint source is $$f_j^{\dagger s}(x,t)=\Sigma_{r=1}^{R_s}[s_i^s(x_r,-t)-d_i^s(x_r,-t)]\delta(x-x_r) \qquad (45)$$

This adjoint source gives rise to the FWI adjoint wavefield $$s_i^{\dagger}(s,t)=\int_{-\infty}^{\infty}\int G_{ij}(x,x',t-t')f_j^{\dagger}(x',t')d^3x'dt' \qquad (48)$$

B. Source-Encoded FWI

If the desired measurement is based on the Fourier coefficients of the full time-series of the seismograms, the observed data $d_i^s(x_r, t)$ are Fourier transformed for all sources $s=1, \ldots S$, recorded by a set of receivers $x_r$, $r=1, \ldots, Rs$, to obtain the Fourier coefficients $d_i(x_r, \omega_s)$, which are evaluated at the encoded frequencies $\omega_s$:

$$d_i^s(x_r)\equiv d_i(x_r,\omega_s) \qquad (49)$$

To ensure that the discrete Fourier transform of the observed data contains exactly the encoded frequencies $\omega_s$, $s=1, \ldots, S$, resampling may be used, such that the new sampling frequency respects the three conditions described above, and zero padding, such that the integral $$d_i^s(x_r) = \frac{1}{k\Delta\tau}\int_0^{k\Delta\tau} d_i(x_r, t)e^{i\omega_s t}dt \qquad (50)$$

can be computed. Here k is the smallest integer such that $k\Delta\tau > T$, where T denotes the length of the unpadded seismogram. It is worth noting that T and $\Delta\tau$ are not correlated. To obtain a good measurement, it is desirable that T captures the full time series. It is not possible to perform any time windowing in seismograms prior to Fourier transformation, because these operations cannot be mimicked in an encoded simulation, that is, windowing requires simulations of individual events.

Next, the encoded waveform cost function is used $$\chi = \frac{1}{2}\sum_{s=1}^{S} \sum_{r=1}^{R_s} [s_i^{s*}(x_r) - d_i^{s*}(x_r)][s_i^s(x_r) - d_i^s(x_r)] \qquad (51)$$

Effectively this cost function is a frequency-domain version of (45) summed over all sources. The options of randomizing the frequency assigned to each source, as well as the option of assigning multiple frequencies to the same source, are discussed. The variation of this encoded cost function may be expressed as $$\delta\chi = \Re\sum_{s=1}^{S}\sum_{r=1}^{R_s}[s_i^{s*}(x_r)-d_i^{s*}(x_r)]\delta s_i^s(x_r) = \qquad (52)$$

$$\Re\sum_{s=1}^{S}\sum_{r=1}^{R_s}\sum_{s'=1}^{S}[s_i^{s*}(x_r)-d_i^{s*}(x_r)]\delta_{ss'}\delta s_i^{s'}(x_r)$$

$$= \Re\frac{1}{\Delta\tau}\int_{T_{ss}}^{T_{ss}+\Delta\tau}\sum_{s=1}^{S}\sum_{r=1}^{R_s}[s_i^{s*}(x_r)-d_i^{s*}(x_r)]$$

$$\exp(-i\omega_s t)\sum_{s'=1}^{S}\delta s_i^{s'}(x_r)\exp(i\omega_{s'}t)dt =$$

$$\Re\frac{1}{\Delta\tau}\int_{T_{ss}}^{T_{ss}+\Delta\tau}\int\sum_{s=1}^{S}\sum_{r=1}^{R_s}[s_i^{s*}(x_r)-d_i^{s*}(x_r)]\delta(x-x_r)$$

$$\exp(-i\omega_s t)\sum_{s'=1}^{S}\delta s_i^{s'}(x)\exp(i\omega_{s'}t)d^3xdt$$

where the orthogonality (30) in the third equality is used. The cost function is given by $$F_j^{\dagger}(x,t)=R\Sigma_{s=1}^{S}f_j^{\dagger s}(x,\omega_s)\exp(i\omega_s t) \qquad (53)$$

where $f_j^{\dagger s}(x, \omega_s)$ denotes the Fourier transform of the classical waveform adjoint source (25) associated with source s. To avoid spectral leakage, it is critical that the Fourier coefficients $d_i^s(x_r)$ and $s_i^s(x_r)$ are evaluated exactly at the source encoded frequencies, not approximated via a narrow bandpass filter.

It is important to note that the encoded super adjoint source (53) may actually be constructed directly from the stationary parts of the encoded forward wavefield, $s_i^s(x_r)$, and the data Fourier coefficients (49), $d_i^s(x_r)$. In other words, the waveform adjoint source may be calculated based on a 'super measurement,' requiring just a single super adjoint calculation.

The 'super' adjoint wavefield $S_i^\dagger(x, t)$ generated by the encoded adjoint source (53) may be expressed in the form $$S_i^\dagger(x,t) = \int_{-\infty}^t \int G_{ij}(x,x'; t-t') F_j^{\dagger s}(x', t') \, d^3x' dt' \quad (54)$$

Thus, like the encoded super forward wavefield (16), the recipe for calculating the encoded super adjoint wavefield is simple: combine all the usual adjoint sources into the source-encoded super adjoint source (53) and run one simulation to obtain the encoded super adjoint wavefield (54).

In anticipation of the Fréchet derivatives, the combined sums over s and r in the misfit variation (52) give rise to the encoded adjoint wavefield (54), whereas the sum over $s^\square$ gives rise to the encoded forward wavefield (38).

vi. Phase, Amplitude, Traveltime, and "Double-Difference" Cost Functions

The choice of measurement and related cost function is a critical component of a successful inversion strategy. In the interest of succinctness, discussions of source-encoded cost functions are relegated, and adjoint sources are related involving phase, amplitude, cross-correlation traveltimes and various 'double-difference' measurements. It was demonstrated that phase, amplitude, and even hybrid (phase+amplitude) measurements are amenable to double-differencing, as opposed to conventional waveform measurements. Double-difference measurements hold great promise for source-encoded adjoint tomography, because they do not require any knowledge of the original source-time function or the instrument response.

vii. Source-Encoded Adjoint Tomography

Suppose there are a set of adjoint sources $f_j^{\dagger s}(x, t)$, $s=1, \ldots, S$, one for each earthquake in the database. These adjoint sources are constructed in the usual fashion based on measurements of the differences between observed and simulated seismograms. To obtain the encoded adjoint wavefield, the classical waveform adjoint sources are combined into an encoded adjoint super source $$F_j^\dagger(x,t) = R\Sigma_{s=1}^S f_j^{\dagger s}(x,\omega_s)\exp(i\omega_s t) \quad (55)$$

Based on this source, the super adjoint wavefield is given by $$S_i^\dagger(x,t) = \int_{-\infty}^t \int G_{ij}(x,x';t-t') F_j^\dagger(x',t') d^3x' dt' \quad (56)$$

viii. Decoding the Encoded Adjoint Wavefield

The super adjoint wavefield simulation (56) is carried out until it reaches a steady state at time $T_{SS}$ and expressed as:

$$S_i^\dagger(x, t) = \sum_{s=1}^S \left[ A_i^{\dagger s}(x)\cos(\omega_s t) - B_i^{\dagger s}(x)\sin(\omega_s t) \right] \quad (57)$$

$$= \Re \sum_{s=1}^S s_i^{\dagger s}(x)\exp(-i\omega_s t)$$

where $$s_i^{\dagger s}(x) = A_i^{\dagger s}(x) - iB_i^{\dagger s}(x) \quad (58)$$

And where the stationary parts $$A_i^{\dagger s}(x) = \Re s_i^{\dagger s}(x) \quad (59)$$

and $$B_i^{\dagger s}(x) = \Im s_i^{\dagger s}(x) \quad (60)$$

May be decoded based on the expressions $$A_i^{\dagger s}(x) = \frac{2}{\Delta\tau} \int_{T_{ss}}^{T_{ss}+\Delta\tau} S_i^\dagger(x, t)\cos(\omega_s t) dt \quad (61)$$

-continued $$B_i^{\dagger s}(x) = \frac{2}{\Delta\tau} \int_{T_{ss}}^{T_{ss}+\Delta\tau} S_i^\dagger(x, t)\sin(\omega_s t) dt \quad (62)$$

ix. Fréchet Derivative

For an isotropic medium, using the adjoint state method, the variation in the encoded cost function may be expressed in the form $$\delta_\chi = \int (\delta \ln \rho K_\rho + \delta \ln \kappa K_\kappa + \delta \ln \mu K_\mu) d^3x \quad (63)$$

where $K_\rho$, $K_\kappa$, and $K_\mu$ denote Frechet derivatives with respect to density $\rho$, bulk modulus $\kappa$, and shear modulus $\mu$, respectively. Based on the encoded forward and adjoint wavefields $S_i(x, t)$ and $S_i^\dagger(x, t)$, these Frechet derivatives are determined as follows, using the density derivative as an example:

$$K_\rho(x) = -\frac{2}{\Delta\tau} \int_{T_{ss}}^{T_{ss}+\Delta\tau} \rho(x) S_i^\dagger(x, -t) \partial_t^2 S_i(x, t) dt \quad (64)$$

$$= \sum_{s=1}^S \omega_s^2 \rho(x) \left[ A_i^{\dagger s}(x) A_i^s(x) + B_i^{\dagger s}(x) B_i^s(x) \right] \quad (65)$$

$$= \Re \sum_{s=1}^S \omega_s^2 \rho(x) s_i^{\dagger s*}(x) s_i^s(x) \quad (66)$$

Note that there is no crosstalk between sources, thanks to the orthogonality (8) of the constituent monochromatic waves. It is important to recognize that one may either calculate the density Frechet derivative by convolving the encoded forward and adjoint wavefields based on the equality (64), effectively a time-domain approach, or one may choose to calculate it by summing the decoded contributions for each source based on either (65) or (66), effectively a frequency-domain approach. Two complementary recipes are presented for the calculation of Frechet derivatives based on these time- and frequency-domain approaches. Similarly, the remaining Frechet derivatives are $$K_\kappa(x) = -\frac{2}{\Delta\tau} \int_{T_{ss}}^{T_{ss}+\Delta\tau} \kappa(x) \left[ \nabla_i S_i^\dagger(x, -t) \right] \left[ \nabla_j S_i(x, t) \right] dt \quad (67)$$

$$= -\sum_{s=1}^S \kappa(x) \left\{ \left[ \nabla_i A_i^{\dagger s}(x) \right] \left[ \nabla_j A_i^s(x) \right] + \left[ \nabla_i B_i^{\dagger s}(x) \right] \left[ \nabla_j B_i^s(x) \right] \right\} \quad (68)$$

$$= -\Re \sum_{s=1}^S \kappa(x) \left[ \nabla_i s_i^{\dagger s*}(x) \right] \left[ \nabla_j s_i^s(x) \right] \quad (69)$$

$$K_\mu(x) = -\frac{2}{\Delta\tau} \int_{T_{ss}}^{T_{ss}+\Delta\tau} 2\mu(x) D_{ij}^\dagger(x, -t) D_{ij}(x, t) dt \quad (70)$$

$$= -\sum_{s=1}^S 2\mu(x) \left\{ \left[ \frac{1}{2}(\nabla_i A_j^{\dagger s} + \nabla_j A_i^{\dagger s}) - \frac{1}{3}\nabla_k A_k^{\dagger s}\delta_{ij} \right] \right. \quad (71)$$

$$\left[ \frac{1}{2}(\nabla_i A_j^s + \nabla_j A_i^s) - \frac{1}{3}\nabla_k A_k^s\delta_{ij} \right] + \left[ \frac{1}{2}(\nabla_i B_j^{\dagger s} + \nabla_j B_i^{\dagger s}) - \right.$$

$$\left. \frac{1}{3}\nabla_k B_k^{\dagger s}\delta_{ij} \right]\left[ \frac{1}{2}(\nabla_i B_j^s + \nabla_j B_i^s) - \frac{1}{3}\nabla_k B_k^s\delta_{ij} \right]\right\}$$

$$= -\Re \sum_{s=1}^S 2\mu(x) D_{ij}^{\dagger s*}(x) D_{ij}^s(x) \quad (72)$$

where $D_{ij}(x, t)$ and $D_{ij}^\dagger(x, t)$ denote the strain deviators associated with the encoded forward and adjoint wavefields, respectively, and where $$D_{ij}^s = \frac{1}{2}(\nabla_i s_j^s + \nabla_j s_i^s) - \frac{1}{3}\nabla_k s_k^s \delta_{ij} \quad (73)$$

-continued

And $$D_{ij}^{\dagger s} = \frac{1}{2}(\nabla_i s_j^{\dagger s} + \nabla_j s_i^{\dagger s}) - \frac{1}{3}\nabla_k s_k^{\dagger s} \delta_{ij} \quad (74)$$

are the corresponding decoded contributions. Further extensions to anisotropic media are straightforward.

x. Attenuation

Interestingly, when using decoding, the calculation of the shear Q kernel no longer requires an additional adjoint simulation. The adjoint source for attenuation may be obtained from the regular adjoint source via the transformation $$f^{\dagger}_{Qj}(x,\omega)=[(2/\pi)\ln(|\omega|/\omega_0)-i\,\mathrm{sgn}(\omega)]f^{\dagger}_j(x,\omega) \quad (75)$$

Consequently, the $Q_\mu$ Fréchet derivative is simply a modification of the $K_\mu$ kernel (72), namely, $$K_{Q_\mu}(x)=R\Sigma_{s=1}^S[(2/\pi)\ln(|\omega_s|/\omega_0)-i\,\mathrm{sgn}(\omega_s)]2\mu(x)D_{ij}^{\dagger s*}(x)D_{ij}^s(x) \quad (76)$$

To avoid decoding, a second encoded adjoint wavefield, $S^{\dagger}_{Qi}(x, t)$, needs to be calculated, driven by $$F^{\dagger}_{Qj}(x,t)=R\Sigma_{s=1}^S[(2/\pi)\ln(|\omega_s|/\omega_0)-i\,\mathrm{sgn}(\omega_s)]f_j^{\dagger s}(x,\omega_s)\exp(i\omega_s t) \quad (77)$$

xi. Methods

The calculation of Frechet derivatives is initiated by combining all earthquakes or shots into a single source-encoded super source (37), followed by simulating the corresponding source-encoded super forward wavefield (38) until it reaches a steady state. The next ingredient involves calculation of the source-encoded super adjoint wavefield (56) until it reaches a steady state. This requires the construction of the source-encoded super adjoint source (55). In this context, in adjoint tomography measurements are made by comparing observed and simulated seismograms in carefully selected time windows, a process that requires the calculation of individual synthetic seismograms for all sources at a cost that scales linearly with the number of sources. In contrast, in classical FWI adjoint sources may be constructed based on the source-encoded Fourier coefficients of the observed and simulated wavefields, effectively involving a single 'super measurement.' The latter may be obtained directly from the source-encoded super forward wavefield, therefore not requiring the calculation of individual synthetic seismograms. Thus, desirably and remarkably, one iteration in the inverse problem requires just two simulations, independent of the number of sources or receivers.

Once the super forward and adjoint wavefields have been calculated, source-encoded Frechet derivatives may be obtained based on one of two mathematically equivalent approaches, one in the time domain and the other in the frequency domain. These two approaches lead to the following options for the calculation of Frechet derivatives.

A. Option I: Frequency-Domain Approach

In the first approach, steady-state, source-encoded forward and adjoint simulations are decoded to obtain a set of stationary fields proportional to the number of sources in the dataset (Eqs. 43, 44, 61, and 62). These stationary parts are subsequently combined to calculate Frechet derivatives by summing their respective contributions (Eqs. 65, 68, and 71). An advantage of this option is that the encoded forward and adjoint wavefields may be calculated simultaneously and independently. Another advantage is that attenuation poses no challenges, because both wavefields are used only in forward time. A disadvantage of this option is that the stationary parts of the encoded wavefields must be computed simultaneously. This requires significant RAM, even assuming that Fourier transforms are performed on the fly and that no time storage of the wavefields is necessary. Each stationary part consists of a 3-D volume of displacement, and the number of such volumes scales linearly with the number of sources, which can run in the thousands. Ultimately, it is of interest to obtain Frechet derivatives, and neither the stationary parts of the wavefields nor their contributions to the Frechet derivatives are of any practical value.

B. Option II. Time-Domain Approach

In the second approach, steady-state source-encoded forward and adjoint wavefields are simply convolved over a time period proportional to the inverse of the frequency bandwidth of interest, thereby directly rendering the Frechet derivatives (Eqs. 64, 67, and 70). In this option, there is no need to decode the encoded forward and adjoint wavefields, nor do intermediary contributions to the misfit gradient need to be calculated or stored. Attractively, this option requires only minor modifications of the currently used adjoint tomography workflow. As in the current workflow, the encoded forward wavefield must be reconstructed during the calculation of the encoded adjoint wavefield so that they may be convolved, a challenge elegantly solved by the wavefield reconstruction algorithm of Komatitsch et al. ((Komatitsch et al., 2016; Geophys. J. Int. 206(3), 1467-1478). It is important to note that in the source-encoded approach, only the super forward wavefield needs to be reconstructed during the calculation of the Frechet derivatives, whereas in the classical approach, this procedure must be executed for every single forward wavefield, that is, for every event in the database. This translates into a significantly smaller amount of I/O, independent of the number of events.

xii. Comparison of Computational Costs

Traditional time-domain FWI or adjoint tomography requires one forward simulation of a chosen duration T per event to capture the seismic arrivals of interest and one adjoint calculation of the same duration to determine the contribution of this event to the gradient. Unless the forward calculation can be stored on disk, the adjoint calculation is twice as expensive as the forward simulation, because the forward wavefield needs to be reconstructed during the adjoint simulation for convolution. In this context, many industrial applications use checkpointing. Thus, for a given event, cumulative seismograms are calculated for a total duration of 3 T, and a total of $$T_{traditional}=3TS \quad (78)$$

simulation time is required for one iteration involving S events.

In source-encoded FWI, one super forward calculation of duration $T_{ss}+\Delta\tau$ is required, followed by one super adjoint calculation of the same duration. The transient part of the forward wavefield, $T_{ss}$, does not need to be reconstructed to compute the sensitivity kernels. Thus, using Eq. (31), a total simulation time of $$T_{encoded} = \underbrace{2(T_{ss}+\Delta\tau)}_{\text{super forward and adjoint}} + \underbrace{\Delta\tau}_{\text{steady super forward reconstruction}} \quad (79)$$

$$= 2T_{ss}+3\Delta\tau$$

$$= 2T_{ss} + \frac{3(S-1)}{f_{max} - f_{min}}$$

is required per source-encoded iteration. The relative reduction in computational cost is $$\frac{T_{traditional}}{T_{encoded}} = \frac{3TS}{2T_{ss} + \frac{3(S-1)}{f_{max} - f_{min}}} \simeq T(f_{max} - f_{min}) \quad (80)$$

where the last equation holds asymptotically for large values of S, that is for a large number of events.

To make measurements in the traditional way before calculating the misfit gradient based on source encoding, then T simulation time needed to be added per event, and thus the cumulative simulation time becomes $$T_{encoded+measurements} = \quad (81)$$
$$\underbrace{\frac{TS}{measurements}}_{} + \underbrace{2(T_{ss} + \Delta\tau)}_{super\ forward\ and\ adjoint} + \underbrace{\Delta\tau}_{steady\ super\ forward\ reconstruction} =$$
$$TS + 2T_{ss} + \frac{3(S-1)}{f_{max} - f_{min}}$$

In this case, the relative reduction in computational cost is $$\frac{T_{traditional}}{T_{encoded+measurements}} = \quad (82)$$
$$\frac{3TS}{TS + 2T_{ss} + \frac{3(S-1)}{f_{max} - f_{min}}} \simeq \frac{1}{\frac{1}{3} + \frac{1}{T(f_{max} - f_{min})}}$$

where the last equation holds asymptotically for large values of S. It was concluded that in this case a 3× speed-up can be achieved. With regards to read/write operations (I/O), to calculate traditional sensitivity kernels, one can (1) store the entire forward wavefield, (2) attempt to reconstruct the forward wavefield with absorbing boundary storage or (3) reconstruct the forward wavefield on the fly based on the parsimonious storage algorithm of Komatitsch et al. (Komatitsch et al., 2016; Geophys. J. Int. 206(3), 1467-1478). In any case, I/O is proportional to the cumulative forward simulation time, $T_{traditional}$. For large meshes, the remaining I/O costs (seismogram writing, adjoint source reading, sensitivity kernel writing, etc.) become negligible. Thus, it gives $$I/O_{traditional} = \alpha T_{traditional} \quad (83)$$

for some suitably chosen proportionality factor α.

For a source encoded simulation, I/O is only required for the sensitivity kernel computation, and does not involve any storage or reconstruction of the transient part of the super forward wavefield. Thus I/O for an encoded simulation is determined by $$I/O_{encoded} = \alpha \frac{3(S-1)}{f_{max} - f_{min}} \quad (84)$$

$$\frac{I/O_{traditional}}{I/O_{encoded}} = \frac{TS(f_{max} - f_{min})}{S-1} \simeq T(f_{max} - f_{min}) \quad (85)$$

Since no forward wavefield storage is required for making measurements, I/O remains basically unchanged, and thus $$I/O_{encoded+measurements} \approx I/O_{encoded} \quad (86)$$

even if the relative I/O cost due to writing individual seismograms may become significant for a large number of events.

Thus, given the duration of a seismogram for making measurements T, the time to reach a steady state $T_{ss}$, and a simulation bandwidth $f_{max} - f_{min}$, Eqs. (78)-(82) and Eqs. (83)-(86) enable us to quantitatively assess the computational benefits of source encoding, as illustrated in FIG. 14.

A case of particular interest involves global FWI. Such computationally demanding tomographic inversions are currently carried out in the 9-150$^s$ period range using databases with hundreds to thousands of earthquakes and three-component seismograms 60-180 min in duration.

Parsimonious storage requirements for kernel calculations involve more than a petabyte of disk space. If traditional measurements are made, the best a 3× speed-up in simulation time can be achieved, as predicted by Eq. (82). The difference is much more significant for I/O, where a 700× reduction in storage requirements was observed. If global FWI could be performed without making individual measurements, which is not a simple proposition, the speed-up would be enormous, approaching factors of 700×.

xiii. Inversion Options and Strategies

In this section, the method and various inversion options and strategies are illustrated. Following Yuan et al. (Yuan, Y. O., et al., Geophys. J. Int., 206(3), 1599-1618), a global Rayleigh-wave phase speed map determined by Trampert & Woodhouse (Trampert, J. & Woodhouse, J. H., 2003. Geophys. J. Int., 154(1), 154-165) was used as the 2-D target model. Designed for didactic purposes, this simplified model is computed on a 180 m×90 m rectangular mesh, with Stacey absorbing boundaries, using the membrane wave propagation solver capability of the SPECFEM2D package (Komatitsch, D. & Tromp, J., 1999. Geophys. J. Int., 139(3), 806-822). In the experiments, a combination of 32 earthquakes and 293 seismographic stations were used. The 'observed' data were simulated using a Ricker wavelet with a 260 Hz central frequency for each event. Each wave simulation ran on a 80×40 spectral-element mesh divided into 8 MPI slices, totaling 52 552 integration points, and using an Intel Xeon CPU E5607 cadenced at 2.27 GHz, and running computations in single precision. To perform the inversions, the SeisFlows framework (Modrak, R. T., et al., 2018.Comput. Geosci., 115, 88-95) and a constant phase speed map of 4500 m s−1 were used as the initial model.

A. Frequency-Domain Encoding

The first experiment is designed to demonstrate the absence of crosstalk between encoded sources in the frequency domain. The result of conventional FWI, described in the section bout Classical FWI, in which sensitivity kernels or 'event kernels' are calculated in the frequency domain for each of the 32 sources and summed to obtain the gradient of the cost function, requiring 64 numerical simulations per iteration. In this case, the gradient is calculated in the frequency domain based on Eq. (72) using one super forward and one super adjoint simulation, that is, just two numerical simulations per iteration. The maximum discrepancy over space of the absolute difference between the two approaches is less than 0.0058 percent.

B. Time-Domain Encoding

In FIG. 16 the same experiment was performed in the time domain. In this case, the gradient is calculated in the time domain based on Eq. (70). The small differences shown in 5(c) demonstrate that frequency-domain decoding is not necessary for the calculation of supersensitivity kernels, thanks to the mathematical equivalence of Eqs. (70) and (72).

C. Decoding

Contributions of individual events were compared to the overall gradient calculated individually and simultaneously, and decoded based on Eqs. (61) and (62). Each of the 32 events is encoded with 512 frequencies, for a total of 16 384 frequencies over the [200;400] Hz bandwidth, using a frequency spacing of 0.012207 Hz. Note that despite the fact that events 1 (200.0 Hz) and 2 (200.012 Hz) are extremely close in frequency, they are still perfectly decoded without crosstalk.

The absolute differences between the individual simulations (first column) and decoded super simulations (second column) are tiny (third column), further demonstrating the absence of cross talk between sources during simultaneous runs. The success of using such massive amounts of encoded frequencies also relies on the accuracy of the wave solver.

FIG. 17 summarizes investigations of the effects of (1) using an incorrect time interval for decoding and (2) decoding a time series that has not yet reached a steady state. In both cases, orthogonality is lost, resulting in an incorrectly decoded signal. Note that it takes 2000 time steps to reach a steady state (defining $T_{ss}$) followed by 1 638 400 time steps of steady state (defining $\Delta\tau$), illustrating the fact that, in general, $T_{ss} \neq \Delta\tau 3$.

D. Comparisons Between Classical and Encoded FWI

FIG. 18 compares a usual full spectrum inversion with a source encoded inversion. The encoded version uses 32 frequencies, one per event, in the 200-400 Hz frequency range. Due to the dramatic reduction in frequency when using source encoding, some oscillations were observed in the 50th iteration source-encoded model, something that was sought to mitigate in the next few experiments.

E. Randomization

The previous test was repeated using randomization of the source frequencies used for each iteration. It was concluded that randomly changing the source frequencies eliminates model oscillations, and an increased convergence rate compared to the previous experiment was observed.

F. Multiple Frequencies Per Source

Another option is to assign more than one frequency per event. In this case, the time interval required for decoding is given by Eq. (33). The relative reduction in computational cost, given by Eq. (80), becomes $$\frac{T_{traditional}}{T_{encoded}} \simeq T(f_{max} - f_{min})/N_f \quad (87)$$

that is, the gain is reduced by a factor $N_f$. Again an increased convergence rate compared to the experiment summarized in FIG. 18 was observed.

G. Effects of Noise

Next, the effects of noise on regular and source encoded inversions were explored. A Gaussian perturbation in phase is added to each frequency in the [50;750] Hz range, with zero mean and a standard deviation of 2Tri, where i denotes a percentage perturbation.

Traditional and source encoded inversions was tested when random noise at levels of 1, 5, 10, 20, and 40 percent is added to the data. Unlike traditional FWI, source-encoded inversions remain stable when more than 10 percent of random noise is added to the data, and both the L2 model and data misfits are reduced in a stable fashion.

H. Variable Number of Receivers

A key benefit of the approach to source encoding is that every source need not be recorded by every receiver. This is basically always the case in real inversions, because some stations may not record a given event, or the data quality of certain receivers may be considered too poor for use in the inversion. To accommodate this situation, a mask must be applied when computing the super adjoint source and the cost function, but no major changes are required. Excellent convergence was demonstrated even when each source is recorded by a different random subset of only 30 percent of the 293 available seismographic stations. The difference in terms of convergence rate relative to an inversion based on the full data set is minimal.

I. Phase, Amplitude, and Double-Difference Measurements

Next, source-encoded inversions were considered based on phase or amplitude measurements. Convergence in model space is slightly slower than source-encoded waveform inversion when using phase measurements, and convergence is even slower when using amplitude measurements. However, using a hybrid approach, combining phase and amplitude measurements, leads to a similar convergence rate as the source-encoded FWI inversion, which used a waveform misfit.

Double-difference measurements help reduce inversion problems related to source uncertainties. the results of a double-difference phase inversion, and the results of a double-difference amplitude inversion. For each event, double differences between all station pairs in the database were taken. The double-difference cost functions behave similarly to their classical counterparts in terms of L2 data and model misfit reduction as a function of iteration number.

J. Attenuation

Figure 15:
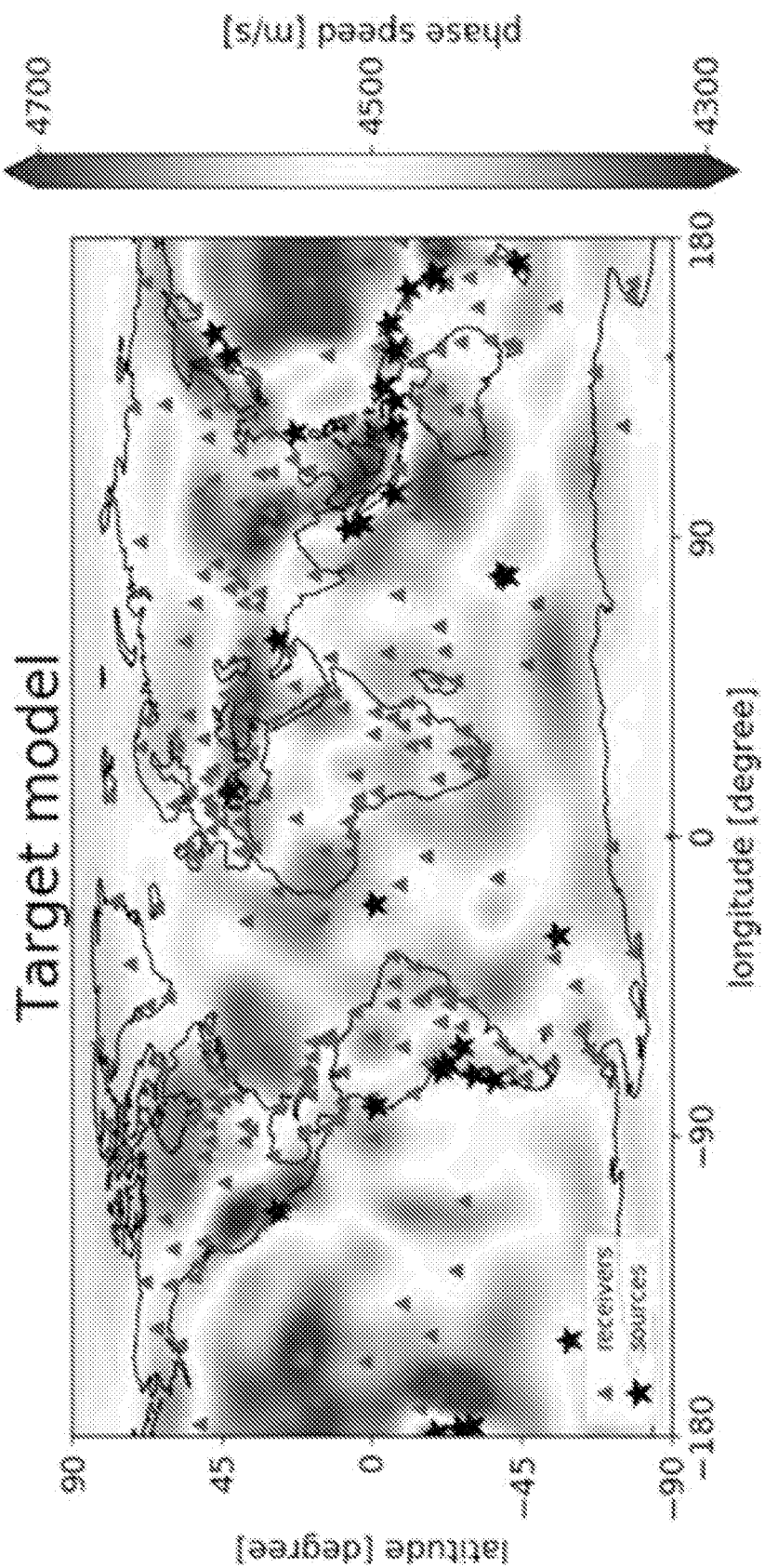
FIG. 15 shows the target model used to illustrate inversion options and strategies. The model is a 50 s Rayleigh wave phase speed map. There are 32 sources labeled by black stars and 293 seismographic stations labeled by green triangles.

Next, a synthetic model that includes the effects of attenuation was considered. The wave speed map, with a reference frequency of 300 Hz, is the same as in FIG. 15. To both illustrate the source encoding efficiency and to better constrain the underlying optimization problem, 1024 events were used. The time domain sensitivity kernel computation with forward wavefield backward reconstruction was used, which is made possible in the presence of attenuation with an implementation of the strategy described in Komatitsch et al. (Komatitsch, D., et al., 2016. Geophys. J. Int., 206(3), 1467-1478). Thanks to the improved coverage, the L2 model misfit of the wave speed decreases more than in the pure wave speed inversion. Global convergence is also obtained for the Q−1 mu map.

K. Offshore Acoustic FWI

To mimick a streamer-type acquisition, 460 acoustic sources are recorded by 600 hydrophones placed to the left of each source, spaced uniformly 10 m below the top of the model. These hydrophones cover 6 km, or less when the source is located less than 6 km from the left side of the model. Unlike in the preceding surface-wave examples, the challenge in this case is recovery of the model from one-sided illumination and acquisition. Each source is encoded with one randomized frequency in the 1-5.6 Hz range, and each super shot involves 120 000 time steps. The resulting speed-up compared to the 20 000 time steps required for a regular simulation is around 77. The resulting model after 400 iterations based on a double-difference phase cost function. As the frequency content of the inverted data increases with each iteration, an increase of the evolving data misfit during the second half of the inversion was observed.

L. Offshore Coupled Acoustic-Elastic FWI

As a second exploration seismology example, the results of a source-encoded inversion for a coupled acoustic-elastic offshore version of the Marmousi model. There are 150 acoustic sources recorded by 500 hydrophones placed 10 m below the top of the water layer, providing one-sided illumination and acquisition. Each source is encoded with two randomized frequencies, using a double-difference phase cost function. The first iteration uses waves in the 1-6 Hz range. At each subsequent iteration, the range is increased by 0.1 Hz until iteration 30. Iterations above 30 are performed in the 4-9 Hz range. Each super shot involves 50 000 time steps, while a nonencoded simulation requires 10 000 time steps, leading to a speed-up of 30. Despite the fact that both the sources and receivers are located near the top of the water layer, the shear wave speed model is reasonably well recovered. Adding a few ocean bottom seismometers would undoubtedly improve the quality of the recovered shear wave speed model, but this is not the objective of this study.

A version of source encoding was developed for explicit time-domain solvers that facilitate the calculation of the gradient of a cost function independent of the number of sources or receivers. The approach does not suffer from crosstalk between different sources, and all receivers do not need to record all sources. To obtain the gradient, source-encoded forward and adjoint wavefields are run until they reach a steady state. At that point, the steady-state fields are either decoded to extract their stationary parts, which are subsequently combined to obtain the full gradient by summing their respective contributions. Alternatively, the steady-state forward and adjoint wavefields are convolved over a time period proportional to the inverse of the encoded frequency spacing, which mathematically results in the same gradient. The second approach involves only minor modifications of the currently used adjoint tomography workflow.

xiv. Conclusion

In adjoint tomography, one generally compares individually observed and simulated seismograms by making measurements in specific time windows. In this approach, the number of numerical simulations required for making measurements and constructing adjoint sources scales linearly with the number of seismic sources, S. Once the synthetics have been calculated, the gradient of the cost function may be calculated based on source encoding in just two additional numerical simulations per iteration, which means that one iteration requires S+2 simulations. The overall computational cost may be reduced to just two simulations per iteration if the measurements needed for the construction of the adjoint sources are based on the source-encoded Fourier coefficients of the observed and simulated seismograms, leading to a single 'super measurement'. It was demonstrated that the latter approach is stable for acoustic and offshore coupled acoustic-elastic FWI.

III. Computing System for Implementing Disclosed Methods

Figure 19:
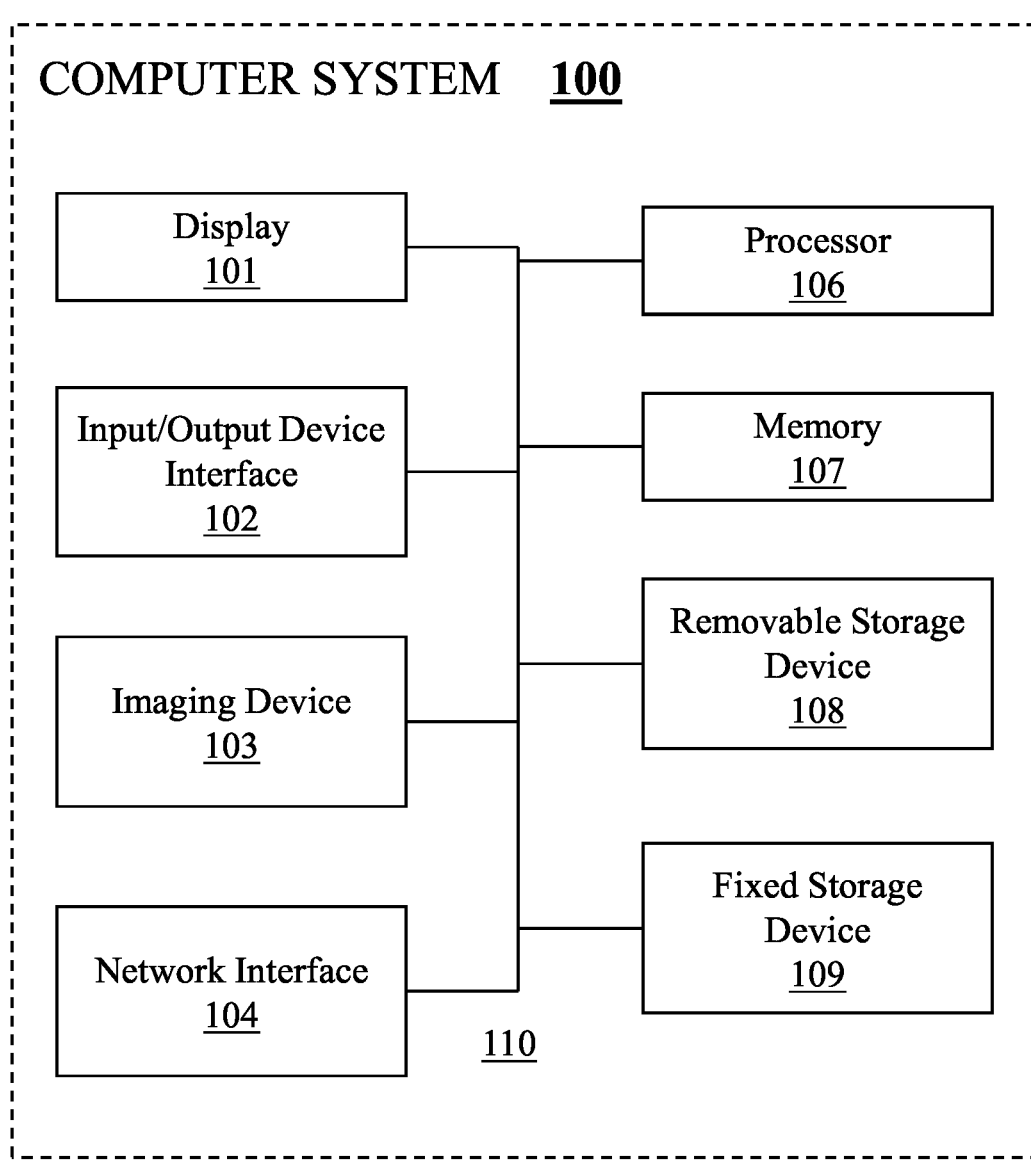
FIG. 19 shows an example computer system for implementing the disclosed systems and methods.

FIG. 19 is a functional diagram illustrating a programmed computer system in accordance with some embodiments. As will be apparent, other computer system architectures and configurations can be used to perform the described methods. Computer system 100, which includes various subsystems as described below, includes at least one microprocessor subsystem (also referred to as a processor or a central processing unit (CPU) 106). For example, processor 106 can be implemented by a single-chip processor or by multiple processors. In some embodiments, processor 106 is a general purpose digital processor that controls the operation of the computer system 100. In some embodiments, processor 106 also includes one or more coprocessors or special purpose processors (e.g., a graphics processor, a network processor, etc.). Using instructions retrieved from memory 107, processor 106 controls the reception and manipulation of input data received on an input device (e.g., image processing device 103, I/O device interface 102), and the output and display of data on output devices (e.g., display 101).

Processor 106 is coupled bi-directionally with memory 107, which can include, for example, one or more random access memories (RAM) and/or one or more read-only memories (ROM). As is well known in the art, memory 107 can be used as a general storage area, a temporary (e.g., scratch pad) memory, and/or a cache memory. Memory 107 can also be used to store input data and processed data, as well as to store programming instructions and data, in the form of data objects and text objects, in addition to other data and instructions for processes operating on processor 106. Also as is well known in the art, memory 107 typically includes basic operating instructions, program code, data, and objects used by the processor 106 to perform its functions (e.g., programmed instructions). For example, memory 107 can include any suitable computer-readable storage media described below, depending on whether, for example, data access needs to be bi-directional or uni-directional. For example, processor 106 can also directly and very rapidly retrieve and store frequently needed data in a cache memory included in memory 107.

A removable mass storage device 108 provides additional data storage capacity for the computer system 100, and is optionally coupled either bi-directionally (read/write) or uni-directionally (read-only) to processor 106. A fixed mass storage 109 can also, for example, provide additional data storage capacity. For example, storage devices 108 and/or 109 can include computer-readable media such as magnetic tape, flash memory, PC-CARDS, portable mass storage devices such as hard drives (e.g., magnetic, optical, or solid state drives), holographic storage devices, and other storage devices. Mass storages 108 and/or 109 generally store additional programming instructions, data, and the like that typically are not in active use by the processor 106. It will be appreciated that the information retained within mass storages 108 and 109 can be incorporated, if needed, in standard fashion as part of memory 107 (e.g., RAM) as virtual memory.

In addition to providing processor 106 access to storage subsystems, bus 1010 can be used to provide access to other subsystems and devices as well. As shown, these can include a display 101, a network interface 104, an input/output (I/O) device interface 102, an image processing device 103, as well as other subsystems and devices. For example, image processing device 103 can include a camera, a scanner, etc.; I/O device interface 102 can include a device interface for interacting with a touchscreen (e.g., a capacitive touch sensitive screen that supports gesture interpretation), a microphone, a sound card, a speaker, a keyboard, a pointing device (e.g., a mouse, a stylus, a human finger), a global positioning system (GPS) receiver, a differential global positioning system (DGPS) receiver, an accelerometer, and/ or any other appropriate device interface for interacting with system 100. Multiple I/O device interfaces can be used in conjunction with computer system 100. The I/O device interface can include general and customized interfaces that allow the processor 106 to send and, more typically, receive data from other devices such as keyboards, pointing devices, microphones, touchscreens, transducer card readers, tape readers, voice or handwriting recognizers, biometrics readers, cameras, portable mass storage devices, and other computers.

The network interface 104 allows processor 106 to be coupled to another computer, computer network, or telecommunications network using a network connection as shown. For example, through the network interface 104, the processor 106 can receive information (e.g., data objects or program instructions) from another network, or output information to another network in the course of performing method/process steps. Information, often represented as a sequence of instructions to be executed on a processor, can be received from and outputted to another network.

An interface card or similar device and appropriate software implemented by (e.g., executed/performed on) processor 106 can be used to connect the computer system 100 to an external network and transfer data according to standard protocols. For example, various process embodiments disclosed herein can be executed on processor 106 or can be performed across a network such as the Internet, intranet networks, or local area networks, in conjunction with a remote processor that shares a portion of the processing. Additional mass storage devices (not shown) can also be connected to processor 106 through network interface 104.

In addition, various embodiments disclosed herein further relate to computer storage products with a computer-readable medium that includes program code for performing various computer-implemented operations. The computer-readable medium includes any data storage device that can store data which can thereafter be read by a computer system. Examples of computer-readable media include, but are not limited to: magnetic media such as disks and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code as produced, for example, by a compiler, or files containing higher level code (e.g., script) that can be executed using an interpreter.

The computer system as shown in FIG. 19 is an example of a computer system suitable for use with the various embodiments disclosed herein. Other computer systems suitable for such use can include additional or fewer subsystems. In some computer systems, subsystems can share components (e.g., for touchscreen-based devices such as smartphones, tablets, etc., I/O device interface 102 and display 101 share the touch-sensitive screen component, which both detects user inputs and displays outputs to the user). In addition, bus 110 is illustrative of any interconnection scheme serving to link the subsystems. Other computer architectures having different configurations of subsystems can also be utilized.

IV. Definitions

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

It should be noted that the roles of source and receiver may be interchanged using the reciprocity theorem of acoustics, elastic wave propagation, and electricity and magnetism. It will be understood throughout, including in the claims, that whenever "source" or "receiver" are referred to, those designations will be understood to include the reverse resulting from application of reciprocity.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%1, 1%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as is indicating any non-claimed element as essential to the practice of the invention. When used in this document, the term "exemplary" is intended to mean "by way of example" and is not intended to indicate that a particular exemplary item is preferred or required.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A system for ultrasound tomography, comprising:
a plurality of sources configured to transmit waves at one or more frequencies within a frequency bandwidth;
one or more receivers configured to receive the waves transmitted by the plurality of sources; and
a processor configured to:
    (a) use a computerized representation of physical property maps of a medium that influence wave propagation;
    (b) model all the sources and the receivers involved in a dataset;
    (c) associate to each of the sources a sinusoidal source time function with a defined frequency of a set of frequencies regularly spaced within a bandwidth of interest; and
    (d) perform a wave propagation simulation where sources are transmitting simultaneously for a time $T_{ss}+k\Delta\tau$, where $T_{ss}$ is a simulation duration for simulated wavefield to reach a steady state, k is an integer>=1, and $\Delta_\tau=1/\Delta_f$
wherein the cost function comprises a source-encoded cost function that integrates contributions from all sources, and
wherein the cost function comprises waveform differences, phase and amplitude measurements, double-difference phase and amplitude measurements, cross-correlation traveltime measurements, or a generic adjoint tomography cost function.

2. The system of claim 1, further comprising an ultrasound wave generator configured to associate each of the sources with a defined frequency $f_s$ of a set of frequencies regularly spaced at $\Delta f$ within a $[f_{min}\ f_{max}]$ bandwidth.

3. The system of claim 1, wherein the processor is further configured to:
    (e) receive observed measurements from at least one sensor based on a wave transmitted from at least one source passing through a medium;
    (f) estimate a frequency-domain observed pressure $\hat{p}_{obs}(x, f_s)$ for each source, where x is a spatial location of a receiver, $f_s$ is a frequency associated with source s;
    (g) evaluate $$\hat{p}_{syn}(x, f_s) = \frac{1}{k\Delta\tau}\int_{T_{ss}}^{T_{ss}+k\Delta\tau} P_{syn}(x, t)e^{-2i\pi f_s(t-T_{ss})}$$

simultaneously for all sources at all receiver positions, where t is time of simulation; and
    (h) estimate a cost function based on the values of $\hat{P}_{obs}$ and $\hat{P}_{syn}$.

4. The system of claim 3, wherein the processor is further configured to:
    (i) evaluate the gradient of the cost function for the bulk modulus κ, as defined by $$K_\kappa(x) = -\frac{2}{\Delta\tau}\int_{T_{ss}}^{T_{ss}+\Delta\tau} \kappa^{-1}(x)\partial_{t^2} P_{syn}^\dagger(x, T_{ss}+\Delta\tau-t)P_{syn}(x,t)dt$$

where $P_{syn}^\dagger$ is an encoded adjoint wavefield, and $\partial_{t_2}$ is a second order partial derivative in time, operator.

5. The system of claim 4, wherein the processor is further configured to repeat steps (d) and (g)-(i) to minimize the cost function.

6. The system of claim 2, wherein the defined frequency $f_s = f_{min}+(s-1)\Delta f$ and $$\Delta f = \frac{f_{max}-f_{min}}{S-1},$$

where s denotes an individual source and S is the total number of sources, $f_s$ is frequency associated with source s, and $[f_{min}\ f_{max}]$ is the bandwidth of interest.

7. The system of claim 1, wherein each source is detected by a different subset of sensors.

8. The system of claim 1, wherein the simulation comprises at least one forward simulation and adjoint simulation per iteration.

9. The system of claim 1, wherein the waves transmitted from the sources are visco-acoustic waves.

10. The system of claim 1, wherein the processor is further configured to evaluate $$\widetilde{p_{syn}}(x_r, f_s; \tau) = \frac{1}{\Delta\tau}\int_\tau^{\tau+\Delta\tau} P_{syn}(x_r, t)e^{-2i\pi f_s(t-\tau)}dt$$

$\forall \{s, r\}, \forall \epsilon, \exists T_{ss}$ such that $\forall \tau > T_{ss}$:

$|\widetilde{p_{syn}}(x_r, f_s; \tau) - \widetilde{p_{syn}}(x_r, f_s; T_{ss})| < \epsilon$ where s represents a given source simulated in simulation, r represents a given receiver, that records a given source s, $x_r$ is the position of the receiver r, t is time of the simulation, r is time after $T_{ss}$, Psyn is a wavefield simulated by a solver, $f_s$ is a frequency associated with source s, and ε can be any value.

11. The system of claim 1, wherein the processor is further configured to compute a gradient of the cost function Xw represented by:

$$\chi w(m) = \frac{1}{2}\sum_{s=1}^{S}\sum_{r=1}^{R_s} |\widehat{p_{syn}}(x_r, f_s; m) - \widehat{p_{obs}}(x_r, f_s)|^2$$

where m is a wavespeed, density, attenuation map, or a combination, $\overline{P_{syn}}$ the Fourier transform of the wavefield $P_{syn}$, and $\overline{P_{obs}}$ is the Fourier transform of the observed wavefield $P_{obs}$.

12. The system of claim 1, wherein the system comprises an ultrasound device.

13. The system of claim 1, wherein the medium comprises human tissue or soil.

14. The system of claim 1, wherein the processor is further configured to generate an image representation of the medium.

15. A method for ultrasound tomography, comprising:
(i) transmitting, by a plurality of sources, waves at one or more frequencies within a frequency bandwidth;
(ii) receiving, by one or more receivers, the waves transmitted by the plurality of sources;
iii) using, by a processor, a computerized representation of physical property maps of a medium that influence wave propagation;
(iv) modeling, by the processor, all the sources and the receivers involved in a dataset;
(v) associating, by the processor, to each of the sources a sinusoidal source time function with a defined frequency of a set of frequencies regularly spaced within a bandwidth of interest; and
(iv) performing, by the processor, a wave propagation simulation where sources are transmitting simultaneously for a time $T_{ss}+k\Delta\tau$, where $T_{ss}$ is a simulation duration for simulated wavefield to reach a steady state, k is an integer >=1, and $\Delta_\tau = 1/\Delta f$
wherein the cost function comprises a source-encoded cost function that integrates contributions from all the sources, and
wherein the cost function comprises waveform differences, phase and amplitude measurements, double-difference phase and amplitude measurements, cross-correlation traveltime measurements, or a generic adjoint tomography cost function.

16. The method of claim 15, further comprising associating each of the sources with a defined frequency $f_s$ of a set of frequencies regularly spaced at $\Delta f$ within a $[f_{min}\ f_{max}]$ bandwidth.

17. The method of claim 15, further comprising:
(v) receiving observed measurements from at least one sensor based on a wave transmitted from at least one source passing through a medium;
(vi) estimating a frequency-domain observed pressure $\hat{p}_{obs}(x, f_s)$ for each source,
where x is a spatial location of a receiver, $f_s$ is a frequency associated with source
(vii) evaluating $$\hat{p}_{syn}(x, f_s) = \frac{1}{k\Delta\tau}\int_{T_{ss}}^{T_{ss}+k\Delta\tau} P_{syn}(x, t)e^{-2i\pi f_s(t-T_{ss})}dt$$

simultaneously for all sources at all receiver positions, where t is time of simulation; and
(viii) estimating a cost function based on the values of $\hat{p}_{obs}$ and $\hat{p}_{syn}$.

18. The method of claim 17, further comprising:
(ix) evaluating the gradient of the cost function for the bulk modulus κ, as defined by $$K_\kappa(x) = -\frac{2}{\Delta\tau}\int_{T_{ss}}^{T_{ss}+\Delta\tau}\kappa^{-1}(x)\partial_{t^2}P_{syn}^\dagger(x, T_{ss}+\Delta\tau-t)P_{syn}(x,t)dt$$

where $P_{syn}^\dagger$ is an encoded adjoint wavefield, and $\partial_{t_2}$ is a second order partial derivative in time, operator.

19. The method of claim 18, further comprising repeating steps (iv) and (vii)-(ix) to minimize the cost function.

20. The method of claim 16, wherein the defined frequency $f_s = f_{min} + (s-1)\Delta f$ and $$\Delta f = \frac{f_{max}-f_{min}}{S-1},$$

where s denotes an individual source and S is the total number of sources, $f_s$ is frequency associated with source s, and $[f_{min}\ f_{max}]$ is the bandwidth of interest.

21. The method of claim 15, wherein each source is detected by a different subset of sensors.

22. The method of claim 15, wherein the simulation comprises at least one forward simulation and adjoint simulation per iteration.

23. The method of claim 15, wherein the waves transmitted from the sources are visco-acoustic waves.

24. The method of claim 15, further comprising evaluating $$\widehat{p_{syn}}(x_r, f_s; \tau) = \frac{1}{\Delta\tau}\int_\tau^{\tau+\Delta\tau} P_{syn}(x_r, t)e^{-2i\pi f_s(t-\tau)}dt$$

$$\forall \{s, r\}, \forall \epsilon, \exists T_{ss} \text{ such that } \forall \tau > T_{ss}:$$

$$|\widehat{p_{syn}}(x_r, f_s; \tau) - \widehat{p_{syn}}(x_r, f_s; T_{ss})| < \epsilon$$

where s represents a given source simulated in simulation, r represents a given receiver, that records a given source s, $x_r$ is the position of the receiver r, t is time of the simulation, τ is time after $T_{ss}$, Psyn is a wavefield simulated by a solver, $f_s$ is a frequency associated with source s, and ε can be any value.

25. The method of claim 15, further comprising computing a gradient of the cost function Xw represented by:

$$\chi w(m) = \frac{1}{2}\sum_{s=1}^{S}\sum_{r=1}^{R_s}|\widehat{p_{syn}}(x_r, f_s; m) - \widehat{p_{obs}}(x_r, f_s)|^2$$

where m is a wavespeed, density, attenuation map, or a combination, $\overline{P_{syn}}$ is the Fourier transform of the wavefield $P_{syn}$, and $\overline{P_{obs}}$ is the Fourier transform of the observed wavefield $P_{obs}$.

26. The method of claim 15, wherein the medium comprises human tissue or soil.

27. The method of claim 15, further comprising generating an image representation of the medium.

* * * * *